(12) United States Patent
Marcin et al.

(10) Patent No.: US 7,338,974 B2
(45) Date of Patent: Mar. 4, 2008

(54) MACROCYCLIC DIAMINOPROPANES AS BETA-SECRETASE INHIBITORS

(75) Inventors: Lawrence R. Marcin, Bethany, CT (US); Andrew C. Good, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 11/501,328

(22) Filed: Aug. 9, 2006

(65) Prior Publication Data
US 2007/0037868 A1 Feb. 15, 2007

Related U.S. Application Data

(60) Provisional application No. 60/707,904, filed on Aug. 12, 2005.

(51) Int. Cl.
C07D 403/04 (2006.01)
C07D 413/04 (2006.01)
A61P 25/28 (2006.01)
A61K 31/4025 (2006.01)

(52) U.S. Cl. ..................... 514/422; 540/456
(58) Field of Classification Search ............... 540/456; 514/422
See application file for complete search history.

(56) References Cited

FOREIGN PATENT DOCUMENTS

| WO | WO 02/100856 | 12/2002 |
|---|---|---|
| WO | WO 03/072535 | 9/2003 |
| WO | WO 2004/013098 | 2/2004 |
| WO | WO 2004/062625 | 7/2004 |
| WO | WO 2005/018545 | 3/2005 |
| WO | WO 2005/049585 | 6/2005 |

OTHER PUBLICATIONS

Hussain, I. et al., "Identification of a Novel Aspartic Protease (Asp 2) as β-Secretase", *Mol. Cell. Neurosci*, (1999) 14: 419-427.
Lin, X. et al., "Human aspartic protease memapsin 2 cleaves the β-secretase site of β-amyloid precursor protein", Proceedings of the National Academy of Sciences of the USA, (2000) 97: 1456-1460.
Ghosh, A.K., et al., "Structure-based design of cycloamide-urethane-derived novel inhibitors of human brain memapsin 2 (β-secreatse)", *Bioorg. & Med. Chem. Letters*, (2005) 15: 15-20.
Jennings, L.D., et al., "Acylguanidines as inhibitors of BACE-1: Variation of pyrrole ring substituents extending into the S1 and S3 pockets", Abstracts of Papers, 230th ACS National Meeting, Washington, D.C., United States, Aug. 28-Sep. 1, 2005.
Luo, Y., et al., "Mice deficient in BACE1, the Alzheimer's β-secretase, have normal phenotype and abolished β-amyloid generation", *Nature Neuroscience* (2001) 4: 231-232.
Roberds, S.L. et al., "BACE knockout mice are healthy despite lacking the primary β-secretase activity in brain: implications for Alzheimer's disease therapeutics", *Human Molecular Genetics* (2001) 10: 1317-1324.

Seiffert, D.; et al., "Presenilin-1 and -2 are molecular targets for γ-secretase inhibitors", *J. Biol. Chem.* (2000) 275, 34086-34091.
Selkoe, D. J., "Alzheimer's Disease: Genes, Proteins, and Therapy", *Physiol. Rev.* (2001) 81, 741-766.
Selkoe, D. J., "Biochemical Analyses of Alzheimer's Brain Lesions lead to the Identification of αβ and its Precursor", *Ann. Rev. Cell Biol.* (1994) 10: 374-403.
Sinha, S., et al., "Purification and cloning of amyloid precursor protein β-secretase from human brain", *Nature*(London) (1999) 402: 537-540.
Solvibile, W.R. et al., "Thiophene acyl guanidines as BACE1 inhibitors", Abstracts of Papers, 230th ACS National Meeting, Washington, D.C., United States, Aug. 28-Sep. 1, 2005.
Stock, J.R., et al., "Acylguanidines as small molecule BACE1 inhibitors: Initial exploration of S1 and S2' pockets", Abstracts of Papers, 230th ACS National Meeting, Washington, D.C., United States, Aug. 28-Sep. 1, 2005.
Sukhdeo, M.N., et al., "Acylguanidines as small molecule BACE1 inhibitors: Optimization of the S1' region", Abstracts of Papers, 230th ACS National Meeting, Washington, D.C., United States, Aug. 28-Sep. 1, 2005.
Thal, D. R., et al., "Two types of Sporadic Cerebral Amyloid Angiopathy", *J. Neuropath. and Exper. Neurology* (2002) 61: 282-293.
Vassar, R., et al., "β-Secretase cleavage of Alzheimer's amyloid precursor protein by the transmembrane aspartic protease BACE", *Science* (1999) 286: 735-741.

(Continued)

Primary Examiner—Bruck Kifle
(74) Attorney, Agent, or Firm—Aldo A. Algieri

(57) ABSTRACT

There is provided a series of novel macrocyclic diaminopropanes of Formula (I) or a stereoisomer; or a pharmaceutically acceptable salt thereof,

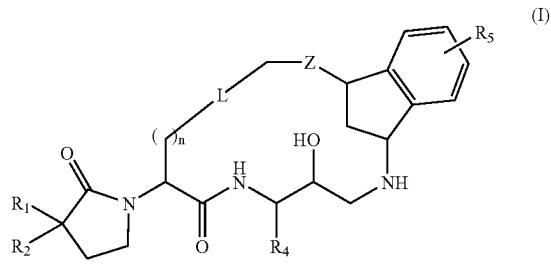

(I)

wherein $R_1$, $R_2$, $R_4$, $R_5$, n, L, Z, and as defined herein, their pharmaceutical compositions and methods of use. These novel compounds inhibit the processing of amyloid precursor protein (APP) by β-secretase and, more specifically, inhibit the production of Aβ-peptide. The present disclosure is directed to compounds useful in the treatment of neurological disorders related to β-amyloid production, such as Alzheimer's disease and other conditions affected by anti-amyloid activity.

8 Claims, No Drawings

OTHER PUBLICATIONS

Walsh, D. M., et al. "Naturally secreted oligomers of amyloid β protein potently inhibit hippocampal long-term potentiation in vivo", *Nature* (2002) 416, 535-539.

Wolfe, M. S., "Secretase Targets for Alzheimer's Disease: Identification and Therapeutic Potential", *J. Med. Chem.* (2001) 44, 2039-2060.

Yan, R. et al., "Membrane-anchored aspartyl protease with Alzheimer's disease β-secretase activity", *Nature* (1999) 402: 533-537.

Zhou, P., et al., "Acylguanidines as small molecule BACE1 inhibitors: Exploration of the S1 pocket", Abstracts of Papers, 230th ACS National Meeting, Washington, D.C., United States, Aug. 28-Sep. 1, 2005.

MACROCYCLIC DIAMINOPROPANES AS BETA-SECRETASE INHIBITORS

CROSS-REFERENCE TO RELATED APPLICATIONS

This is a non-provisional application which claims the benefit of U.S. Provisional Application No. 60/707,904 filed Aug. 12, 2005.

FIELD OF THE DISCLOSURE

This patent application provides novel macrocyclic diaminopropane compounds having drug and bio-affecting properties, their pharmaceutical compositions and method of use. In particular, the disclosure is concerned with a series of novel macrocyclic diaminopropanes which are inhibitors of the β-amyloid peptide (β-AP) production, thereby acting to prevent the accumulation of amyloid protein deposits in the brain and, therefore, are useful in the treatment of neurological disorders related to β-amyloid production. More particularly, the present disclosure relates to the treatment of Alzheimer's Disease (AD) and similar diseases.

BACKGROUND

Alzheimer's Disease is a progressive, neurodegenerative disorder characterized by memory impairment and cognitive dysfunction. AD is characterized pathologically by the accumulation of senile (neuritic) plaques, neurofibrillary tangles, amyloid deposition in neural tissues and vessels, synaptic loss, and neuronal death. It is the most common form of dementia and it now represents the third leading cause of death after cardiovascular disorders and cancer. The cost of Alzheimer's Disease is enormous (in the U.S., greater than $100 billion annually) and includes the suffering of the patients, the suffering of families, and the lost productivity of patients and caregivers. As the longevity of society increases, the occurrence of AD will markedly increase. It is estimated that more than 10 million Americans will suffer from AD by the year 2020, if methods for prevention and treatment are not found. Currently, AD is estimated to afflict 10% of the population over age 65 and up to 50% of those over the age of 85. No treatment that effectively prevents AD or reverses the clinical symptoms and underlying pathophysiology is currently available (for review see Selkoe, D. J. *Ann. Rev. Cell Biol.* 1994, 10, 373-403).

Histopathological examination of brain tissue derived upon autopsy or from neurosurgical specimens in affected individuals reveals the occurrence of amyloid plaques and neurofibrillar tangles in the cerebral cortex of such patients. Similar alterations are observed in patients with Trisomy 21 (Down's syndrome). Biochemical and immunological studies reveal that the dominant proteinaceous component of the amyloid plaque is an approximately 4.2 kilodalton (kD) protein of about 39 to 43 amino acids. This protein is designated Aβ,β-amyloid peptide, and sometimes β/A4; referred to herein as Aβ. In addition to its deposition in amyloid plaques, Aβ is also found in the walls of meningeal and parenchymal arterioles, small arteries, capillaries, and sometimes, venules. Compelling evidence accumulated during the last decade reveals that Aβ is an internal polypeptide derived from a type 1 integral membrane protein, termed β-amyloid precursor protein (APP) (Selkoe, D. *Physiol. Rev.* 2001, 81, 741-766; Wolfe, M. *J. Med. Chem.* 2001, 44, 2039-2060). βAPP is normally produced by many cells both in vivo and in cultured cells, derived from various animals and humans. Several proteolytic fragments of APP are generated by proteinases referred to as secretases. A subset of these proteolytic fragments, designated β-amyloid peptide (Aβ), contains 39 to 43 amino acids and is generated by the combined action of β-secretase and γ-secretase. β-secretase is a membrane-bound, aspartyl protease that forms the N-terminus of the Aβ peptide. The C-terminus of the Aβ peptide is formed by γ-secretase, an apparently oligomeric complex that includes presenilin-1 and/or presenilin-2. Presenilin-1 and presenilin-2 are polytopic membrane-spanning proteins that may contain the catalytic components of γ-secretase (Seiffert, D.; Bradley, J. et al., *J. Biol. Chem.* 2000, 275, 34086-34091).

In addition to AD, excess production and/or reduced clearance of Aβ causes cerebral amyloid angiopathy (CAA) (reviewed in Thal, D., Gherbremedhin, E. et al., *J. Neuropath. Exp. Neuro.* 2002, 61, 282-293). In these patients, vascular amyloid deposits cause degeneration of vessel walls and aneurysms that may be responsible for 10-15% hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients.

A logical approach to reducing AD levels is to interfere with the action of the secretases that are directly involved in the cleavage of APP to AD. The β-secretase enzyme (BACE) is responsible for cleaving APP and forms the amino-terminus of Aβ, initiating the amyloidogenic pathway. The BACE enzyme is a transmembrane aspartyl protease and was described in the literature by several independent groups [see Hussain, I. et al., *Mol. Cell. Neurosci.*, 1999, 14, 419-427; Lin, X. et al., *Proceedings of the National Academy of Sciences of the United States of America* 2000, 97: 1456-1460; Sinha, S., et al., *Nature* 1999, 402, 537-540; Vassar, R., et al., *Science* 1999, 286, 735-741; Walsh, D. M., et al., *Biochemical Transactions* 2002, 30, 552-557; Wolfe, M. *J. Med. Chem.* 2001, 44, 2039-2060; Yan, R. et al., *Nature* 1999, 402, 533-537].

Removal of BACE activity in mice by gene targeting completely abolishes Aβ production [see Luo, Y., et al., *Nature Neuroscience* 2001, 4, 231-232; Roberds, S. L., et al., *Human Molecular Genetics* 2001, 10, 1317-1324]. BACE −/− mice also show no detectable negative phenotypes, suggesting that disruption of BACE-mediated cleavage of APP does not produce additional undesired effects. This demonstrates that a drug substance capable of inhibiting β-secretase activity should lower or halt the synthesis of Aβ and should provide a safe treatment for Alzheimer's disease.

PCT Publication WO 2005049585, published Jun. 2, 2005 discloses novel macrocyclic lactams for the treatment of neurological and vascular disorders related to β-amyloid generation and/or aggregation.

PCT Publication WO 2005018545 A2, published Mar. 3, 2005 discloses macrocyclic BACE inhibitors for the treatment of Alzheimers.

Published article Ghosh, A. K. et al., *Bioorganic and Medicinal Chem. Lett.* 2005, 15, 15-20 discloses macrocyclic amide-urethane inhibitors of BACE.

PCT Publication WO 2004062625 A2, published Jul. 29, 2004 discloses macrocyclic BACE inhibitors for the treatment of Alzheimers.

PCT Publication WO 2002100856 A1, published Dec. 19, 2002 discloses macrocycles useful in the treatment of Alzheimers.

PCT Publication WO 2004013098, published Feb. 12, 2004, discloses lactam derivatives as beta-secretase inhibitors.

PCT Publication WO 2003072535, published Sep. 4, 2003, discloses substituted hydroxyethylamines in the treatment of Alzheimer's Disease.

At present there remains an urgent need to develop pharmaceutical agents capable for effective treatment in halting, slowing, preventing, and/or reversing the progression of Alzheimer's disease. Compounds that are effective inhibitors of beta-secretase, that inhibit beta-secretase mediated cleavage of APP, that are effective inhibitors of Aβ protein production by beta-secretase, and/or are effective in reducing soluble Aβ protein, amyloid beta deposits or amyloid beta plaques, are needed for effective treatment in halting, slowing, preventing, and/or reversing neurological disorders related to Aβ protein production, such as Alzheimer's disease.

SUMMARY OF THE DISCLOSURE

A series of macrocyclic diaminopropanes having the Formula (I)

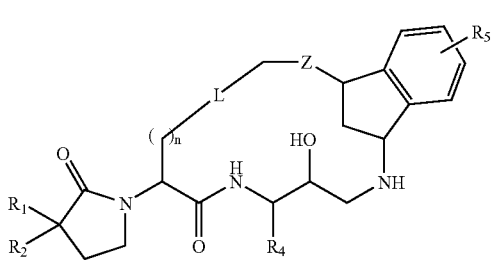

or a stereoisomer; or a pharmaceutically acceptable salt thereof, wherein $R_1$, $R_2$, $R_4$, $R_5$, n, L and Z as defined below are effective inhibitors of the production of β-amyloid peptide (β-AP) from β-amyloid precursor protein (β-APP). The pharmacologic action of these compounds makes them useful for treating conditions responsive to the inhibition of β-AP in a patient; e.g., Alzheimer's Disease (AD) and Down's Syndrome. Therapy utilizing administration of these compounds or a pharmaceutical composition containing a therapeutically effective amount of at least one of these compounds to patients suffering from, or susceptible to, these conditions involves reducing β-AP available for accumulation and deposition in brains of these patients.

DETAILED DESCRIPTION

The present application comprises compounds of Formula I, their pharmaceutical formulations, and their use in inhibiting β-AP production in patients suffering from or susceptible to AD or other disorders resulting from β-AP accumulation in brain tissue. The compounds of Formula I which include stereoisomers and pharmaceutically acceptable salts thereof have the following formula and meanings:

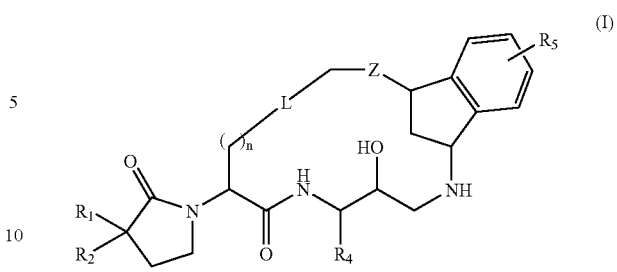

wherein $R_1$ is hydrogen, $C_{1-6}$alkyl or $NHR_3$;

$R_2$ is hydrogen, $C_{1-6}$alkyl, $C_{3-6}$alkenyl, $C_{3-6}$cycloalkyl or $C_{3-6}$cyloalkyl($C_{1-4}$alkyl) in which each group is optionally substituted with a group selected from halogen, $CF_3$, $CF_2H$, OH, $OCF_3$ and $C_{1-4}$alkoxy;

$R_3$ is —C(=O)$R_9$, —C(=O)O$R_9$, —C(=O)NH$R_9$, or $C_{1-6}$alkyl optionally substituted with a group selected from $C_{3-6}$cycloalkyl, halogen, $CF_3$, $OCF_3$, OH, $C_{1-4}$alkoxy and CN;

$R_4$ is $C_{1-6}$alkyl, phenyl or phenyl($C_{1-4}$alkyl) in which each group is optionally substituted with one to two groups selected from halogen, $C_{1-4}$alkyl, OH, $CF_3$, $OCF_3$ and CN;

$R_5$ is hydrogen, halogen, $C_{1-4}$alkyl, OH, $C_{1-4}$alkoxy, $CF_3$, $CF_2H$, $OCF_3$ or CN;

n is 0, 1 or 2;

Z is O or $NR_6$;

$R_6$ is hydrogen or $C_{1-4}$alkyl;

L is —CH($R_7$)—CH($R_8$)— or —C($R_7$)=C($R_8$)—; and $R_7$ and $R_8$ are each independently hydrogen or methyl; and $R_9$ is $C_{1-4}$alkyl optionally substituted with the group selected from halogen, OH, $CF_3$, $NH_2$ and $C_{1-4}$alkoxy;

or a nontoxic pharmaceutically acceptable salt thereof.

The present application also provides a method for the treatment or alleviation of disorders associated with β-amyloid peptide, especially Alzheimer's Disease, cerebral amyloid angiopathy and Down's Syndrome, which comprises administering together with a conventional adjuvant, carrier or diluent a therapeutically effective amount of a compound of Formula (I) or a pharmaceutically acceptable salt thereof.

As used herein, the term "Aβ" denotes the protein designated Aβ, β-amyloid peptide, and sometimes β/A4, in the art. Aβ is an approximately 4.2 kilodalton (kD) protein of about 39 to 43 amino acids found in amyloid plaques, the walls of meningeal and parenchymal arterioles, small arteries, capillaries, and sometimes, venules. The isolation and sequence data for the first 28 amino acids are described in U.S. Pat. No. 4,666,829. The 43 amino acid sequence is well known in the art, see Dingwall, C. Journal of Clinical Investigation 2001, 108, 1243-1246; as well as PCT international patent application WO 01/92235, published Dec. 6, 2001, herein incorporated by reference in its entirety.

The term "APP", as used herein, refers to the protein known in the art as β amyloid precursor protein. This protein is the precursor for Aβ and through the activity of "secretase" enzymes, as used herein, it is processed into Aβ. Differing secretase enzymes, known in the art, have been designated β secretase, generating the N-terminus of Aβ, α secretase cleaving around the 16/17 peptide bond in Aβ, and "γ secretases", as used herein, generating C-terminal Aβ fragments ending at position 38, 39, 40, 42, and 43 or generating C-terminal extended precursors which are subsequently truncated to the above polypeptides.

The term "substituted," as used herein and in the claims, means that any one or more hydrogens on the designated atom is replaced with a selection from the indicated group, provided that the designated atom's normal valency is not exceeded, and that the substitution results in a stable compound.

As used herein and in the claims, "alkyl" or "alkylene" is intended to include both branched and straight-chain saturated aliphatic hydrocarbon groups having the specified number of carbon atoms; for example, "$C_{1-6}$ alkyl" and "$C_{1-10}$ alkyl" denotes alkyl having 1 to 6 or 1 to 10 carbon atoms. Examples of alkyl include, but are not limited to, methyl, ethyl, n-propyl, i-propyl, n-butyl, i-butyl, sec-butyl, t-butyl, pentyl, hexyl, octyl and decyl. Preferred "alkyl" group, unless otherwise specified, is "$C_{1-4}$ alkyl". Additionally, unless otherwise specified, "propyl" denotes n-propyl or i-propyl; "butyl" denotes n-butyl, i-butyl, sec-butyl, or t-butyl.

As used herein and in the claims, "alkenyl" or "alkenylene" is intended to include hydrocarbon chains of either a straight or branched configuration and one or more unsaturated carbon-carbon bonds which may occur in any stable point along the chain, for example, "$C_{2-6}$ alkenyl" include but are not limited to ethenyl, 1-propenyl, 2-propenyl, 1-butenyl, 2-butenyl, 3-butenyl, 3-methyl-2-butenyl, 2-pentenyl, 3-pentenyl, hexenyl, and the like.

As used herein and in the claims, "alkynyl" or "alkynylene" is intended to include hydrocarbon chains of either a straight or branched configuration and one or more carbon-carbon triple bonds which may occur in any stable point along the chain, for example, "$C_{2-6}$ alkynyl" include but not limited to ethynyl, 1-propynyl, 2-propynyl, 1-butynyl, 2-butynyl, 3-butynyl, and the like.

"Alkoxy" or "alkyloxy" represents an alkyl group as defined above with the indicated number of carbon atoms attached through an oxygen bridge. Examples of alkoxy include, but are not limited to, methoxy, ethoxy, n-propoxy, i-propoxy, n-butoxy, s-butoxy, t-butoxy, n-pentoxy, and s-pentoxy. Preferred alkoxy groups are methoxy, ethoxy, n-propoxy, i-propoxy, n-butoxy, s-butoxy, t-butoxy.

As used herein and in the claims, "halogen" refers to fluoro, chloro, bromo, and iodo. Unless otherwise specified, preferred halogens are fluoro and chloro. "Counterion" is used to represent a small, negatively charged species such as chloride, bromide, hydroxide, acetate, sulfate, and the like.

"Cycloalkyl" is intended to include saturated ring groups, having the specified number of carbon atoms. For example, "$C_{3-6}$ cycloalkyl" denotes such as cyclopropyl, cyclobutyl, cyclopentyl and cyclohexyl.

The compounds described herein may have asymmetric centers. An example of a preferred stereochemical configuration is the isomer:

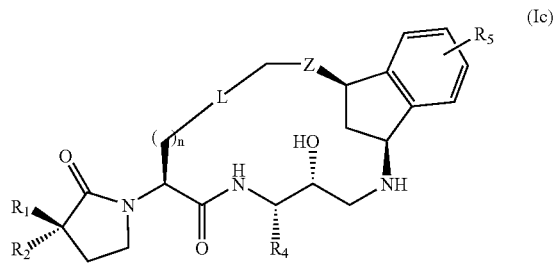

(Ic)

or pharmaceutically acceptable salt thereof, but is not intended to be limited to this example. It is understood, that whether a chiral center in an isomer is "R" or "S" depends on the chemical nature of the substituents of the chiral center. All configurations of compounds of the invention are considered part of the invention. Additionally, the carbon atom to which $R_1$ and $R_2$ is attached may describe a chiral carbon. Compounds of the present disclosure containing an asymmetrically substituted atom may be isolated in optically active or racemic forms. It is well known in the art how to prepare optically active forms, such as by resolution of racemic forms or by synthesis from optically active starting materials. Mixtures of isomers of the compounds of the examples or chiral precursors thereof can be separated into individual isomers according to methods which are known per se, e.g. fractional crystallization, adsorption chromatography or other suitable separation processes. Resulting racemates can be separated into antipodes in the usual manner after introduction of suitable salt-forming groupings, e.g. by forming a mixture of diastereosiomeric salts with optically active salt-forming agents, separating the mixture into diastereomeric salts and converting the separated salts into the free compounds. The enantiomeric forms may also be separated by fractionation through chiral high pressure liquid chromatography columns. Many geometric isomers of olefins and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The phrase "nontoxic pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein and in the claims, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

In the method of the present application, the term "therapeutically effective amount" means the total amount of each active component of the method that is sufficient to show a meaningful patient benefit, i.e., healing of acute conditions characterized by inhibition of β-amyloid peptide production. When applied to an individual active ingredient, administered alone, the term refers to that ingredient alone. When applied to a combination, the term refers to combined amounts of the active ingredients that result in the therapeutic effect, whether administered in combination, serially or simultaneously. The terms "treat, treating, treatment" as used herein and in the claims means preventing or ameliorating diseases associated with β-amyloid peptide.

In general, the macrocyclic diaminopropanes represented by Formula Ia (General Reaction Scheme A) can be prepared by metal catalyzed hydrogenation of the corresponding macrocyclic alkenes represented by Formula Ib. The macrocyclic alkenes Ib can be obtained by ring-closing metathesis (RCM) of diene intermediate 2. Intermediate 2 can be obtained by coupling, under standard conditions known to one skilled in the art, a substituted γ-lactam acid 4 and a substituted 2-hydroxy-1-3-diaminopropane 3. The preparations of γ-lactam acids 4 (General Reaction Scheme B) and substituted 2-hydroxy-1-3-diaminopropanes 3 (General Reaction Scheme C) are disclosed in detail in the discussion given below.

General Reaction Scheme A

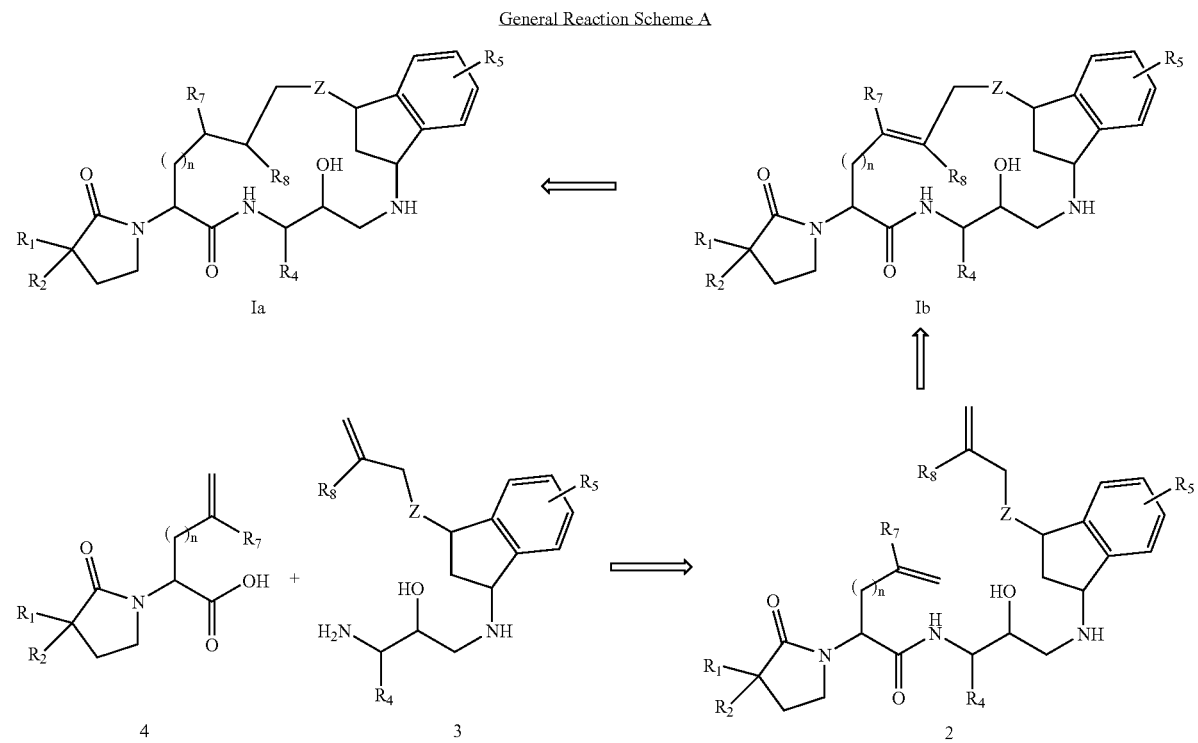

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

In general, the γ-lactam acids 4, for n=1 or 2, can be prepared by alkylation and hydrolysis of the corresponding γ-lactam esters 5 (General Reaction Scheme B). Methods for the synthesis of γ-lactam esters 5, from intermediates such as compound 12, are known to one skilled in the art and are disclosed in a number of references including but not limited to those given below. The γ-lactam acids 4, when n=0, may be prepared from γ-lactams 7 by basic hydrolysis of the methyl ester, oxidation of the methyl sulfide to the corresponding methyl sulfoxide, and subsequent β-hydride elimination of the sulfoxylmethyl group. According to the method of Ates, C. et al., γ-lactams 7 may be prepared by alkylation of an amino acid (i.e. methoinine 11) with ethyl-4-bromobutyrates 10, followed by subsequent ring closure of intermediates 8 using heat and catalytic 2-pyridinol (Ates, C.; Surtees, J.; Burteau, A.-C.; Marmon, V.; Cavoy, E. PCT International Publication WO 03/014080 A2). Methods for the synthesis of ethyl-4-bromobutyrates 9 are known to one skilled in the art and are disclosed in a number of references including but not limited to those given below (Ibarzo, J. and Ortuño, R. M. *J. Org. Chem.* 2001, 66, 4206.).

General Reaction Scheme B

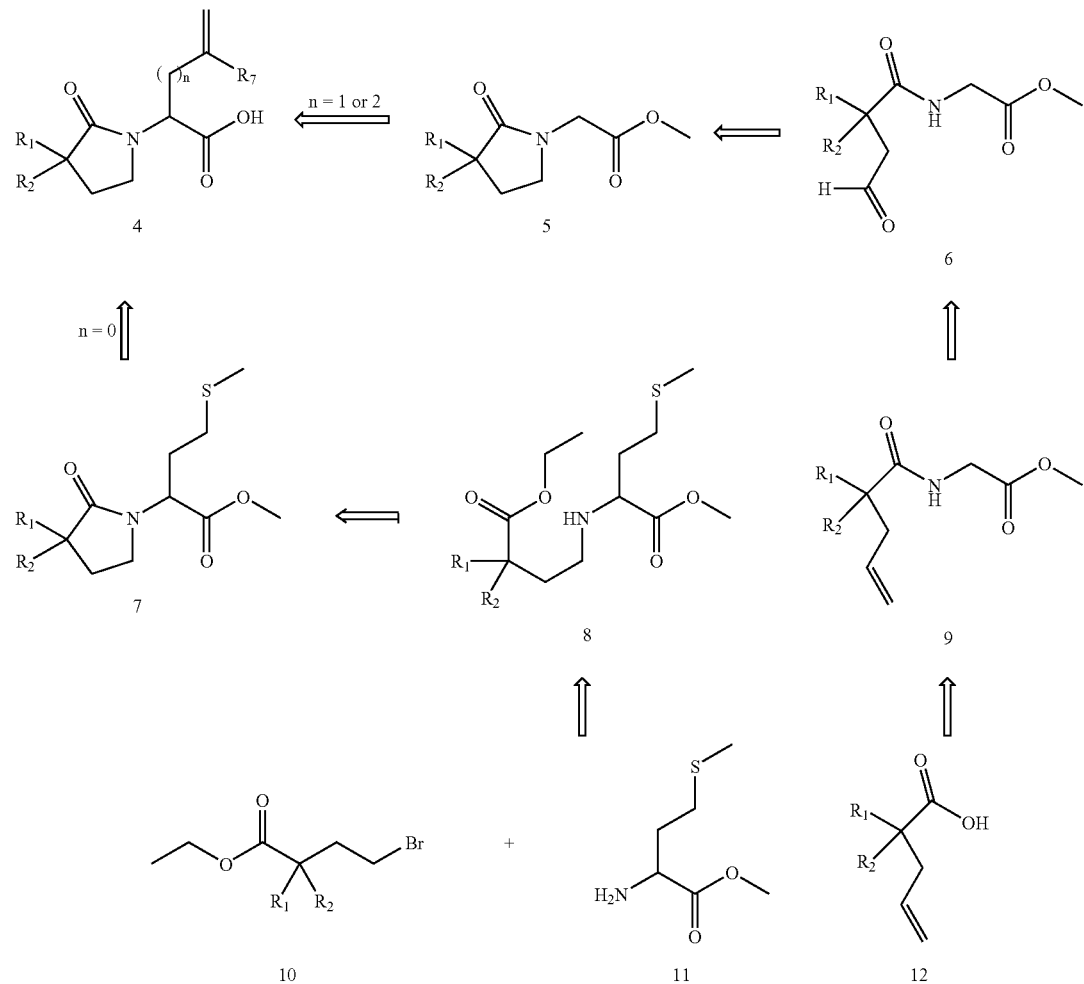

In general, 2-hydroxy-1-3-diaminopropanes 3 can be prepared from N-protected α-amino epoxides 13 and amino indanes 14 (General Reaction Scheme C). The synthesis of N-protected α-amino epoxides 13 from activated amino esters is known to one skilled in the art and is disclosed in a number of references including but not limited to those given below. The synthesis of substituted aminoindanes 14 from 3-aminoindan-1-ones 15 is disclosed in detail in the discussion given below.

General Reaction Scheme C

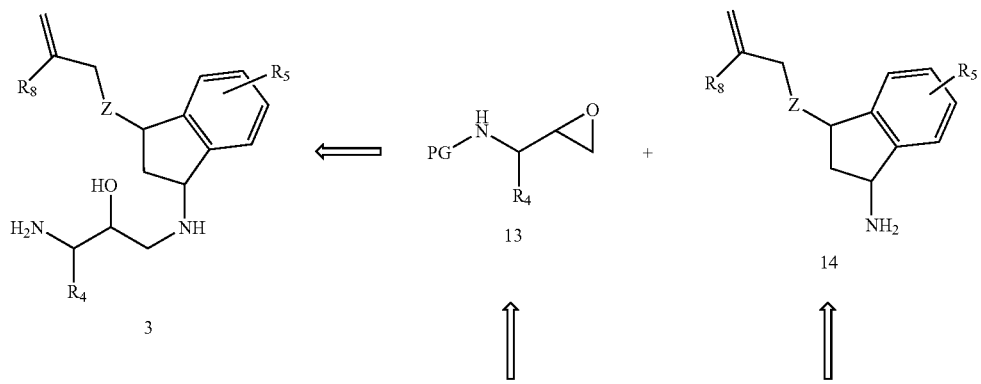

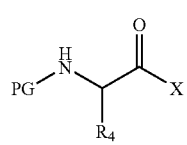

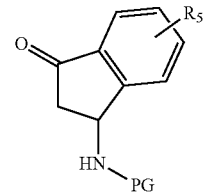

A preferred subset of lactams of formula 4 are represented by formula S-4a (Scheme 1) and are known as monosubstituted γ-lactams. A variety of alpha-allyl carboxylic acids 12a are available utilizing known asymmetric alkylation methodology (for a review, see: Jones, S. *J. Chem. Soc. Perkins I* 2002, 1-21.). Evan's asymmetric alkylation methodology employing N-acyloxazolidinones has proven particularly useful to prepare these alpha-allyl acids [(a) Munoz, L. et. al. *J. Org. Chem.* 2001, 66, 4206. (b) Evans, D. A. et. al. *J. Org. Chem.* 1999, 64, 6411.]. The alpha-allyl carboxylic acids 12a may be coupled under standard conditions to glycine methyl ester using standard coupling reagents reagents like HATU (O-(7-azabenzotriazol-1-yl)-1,1,3,3,-tetramethyluronium hexafluorophosphate), PyBOP (benzotriazole-1-yl-oxy-tris-pyrrolidino-phosphonium hexafluorophosphate), or EDC (1-(3-dimethylaminopropyl)-3-ethylcarbodiimide hydrochloride)/HOBt (1-hydroxybenzotriazole hydrate) in the presence of a tertiary amine base such as triethylamine, N,N-diisopropylethylamine (DIEA), or N-methylmorpholine. Oxidation of the allyl group using ozonolysis or osmium tetroxide/sodium periodate gives an intermediate aldehyde 6a which is cyclized to the γ-lactam 5a using triethylsilane and trifluoroacetic acid (Holladay, M. W.; Nadzan, A. M. *J. Org. Chem.* 1991, 56, 3900-3905; Duan, J. PCT International Publication WO 0059285, 2000). The γ-lactams 5a can be deprotonated using one equivalent of a strong base, such as lithium bis(trimethylsilyl)amide, and alkylated with electrophiles, such as allylbromide, allyliodide, 4-bromo-1-butene, or 3-bromo-2-methylpropene to afford products 18 as mixtures of two diastereomers. When $R_2 \neq H$, the product diastereomers R-18 and S-18 can be separated using silica gel column chromatography or reverse phase HPLC. When $R_2 = H$, the enantiomers can be separated using chiral HPLC methods. The corresponding γ-lactams acids S-4-a can be obtained through basic hydrolysis of the esters S-18.

Scheme 1

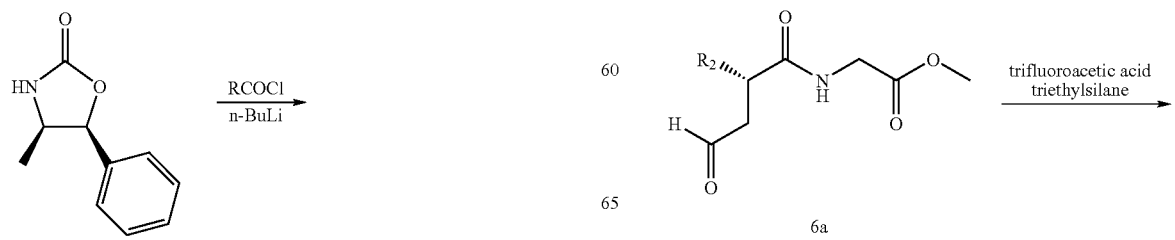

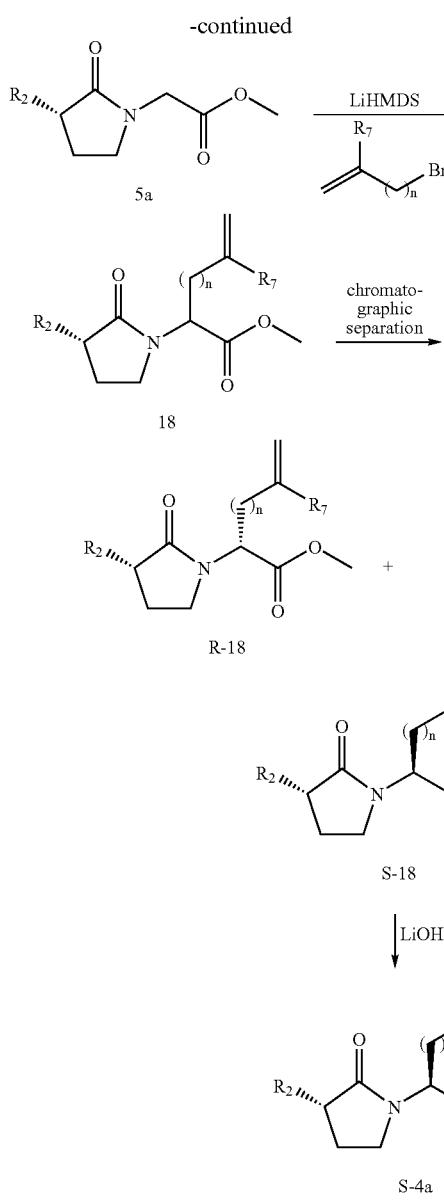

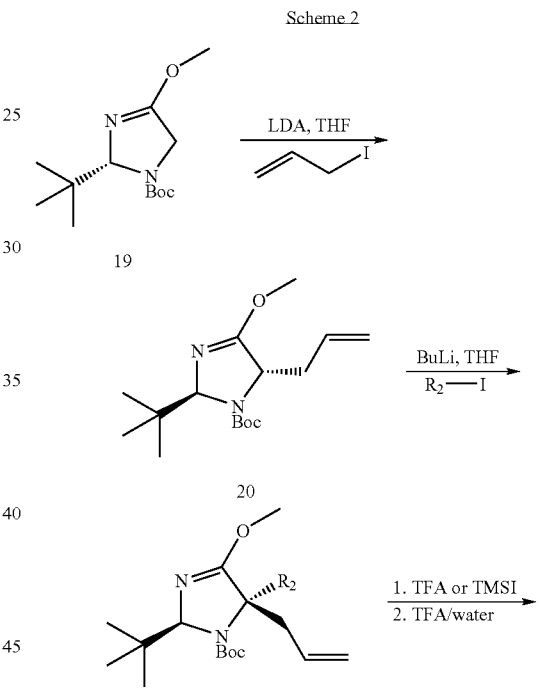

*Journal of Organic Chemistry* 1998, 1337-1351. Hoffmann, M.; Blank, S.; Seebach, D.; Kusters, E.; Schmid, E. *Chirality* 1998, 10, 217-222. Hoffmann, M.; Seebach, D. *Chimia* 1997, 51, 90-92. Blank, S.; Seebach, D. *Angew. Chem.* 1993, 105, 1780-1781.), where (R)- or (S)-2-tert-butyl-4-methoxy-2,5-dihydro-1,3-imidazole-1-carboxylate 19 is alkylated sequentially with allyl iodide and a $R_2$-group electrophile (which can be suitably protected by one skilled in the art if necessary) to provide, with high diastereoselectivity, a protected amino acid equivalent 21. The scalemic amino acid methyl ester 22 is then generated by deprotection of the Boc group and acidic deprotection of the trimethylacetyl acetal. The amine functionality of intermediate 22 can then be protected under standard conditions with protecting groups well known to those skilled in the art, such as t-butyloxycarbonyl (Boc) or benzyloxycarbonyl (Cbz). The free carboxylic acid 12b, can be obtained by saponification of the methyl ester 22.

Another preferred subset of lactams of formula 4 are represented by formula S-4b and are known as disubstituted γ-lactams. Disubstituted γ-lactams

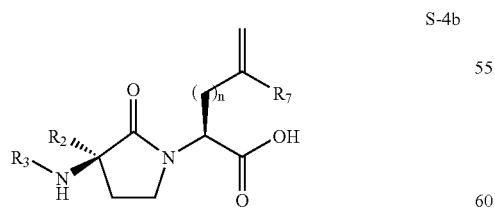

4b can be prepared from substituted quaternary α-allyl amino acids 12b. Synthesis of a substituted quaternary α-allyl amino acid 12b is carried out according to one of several literature methods. Scheme 2 shows the method of Seebach, et. al., (Seebach, D.; Hoffmann, M. *European*

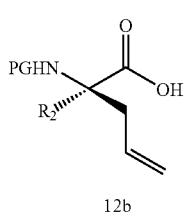

Alternatively, quaternary amino acids can be synthesized from the corresponding amino acid (Scheme 3). Using isoleucine as an example, formation of the benzylidene imine 23 followed by cyclization with benzyloxycarbonyl chloride provides a protected amino acid precursor 24 (Seebach, D.; Fadel, A. *Helv. Chim. Acta.* 1985, 68, 1243; Altmann, E.; Nebel, K.; Mutter, M. *Helv. Chim, Acta* 1991, 74, 800; De, B.; Dellaria, J. F.; Baker, W. R.; Zydowsky, T. M.; Rosenberg, S. H. et al., EP 365992, 1990). Alkylation with allyl bromide or iodide provides the alkylated lactone 25 which can be deprotected under basic conditions to provide the protected amino acid derivative 26.

An additional method for the preparation of quaternary amino acids is shown in Scheme 4. Treatment of a natural or unnatural amino acid 27 with allyl bromide in the presence of $Cs_2CO_3$ provides the amino acid allylic ester 28. Ester enolate Claisen rearrangement of 28 results in 12c (Kazmaier, U. and Maier, S. *Tetrahedron* 1996, 52, 941).

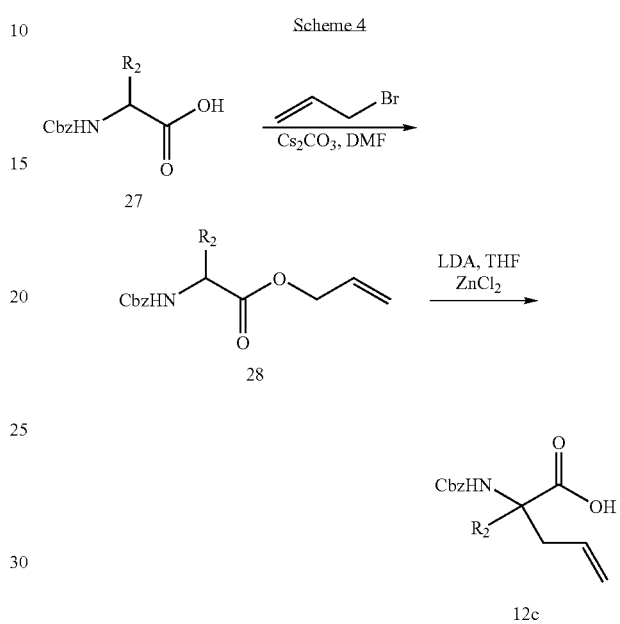

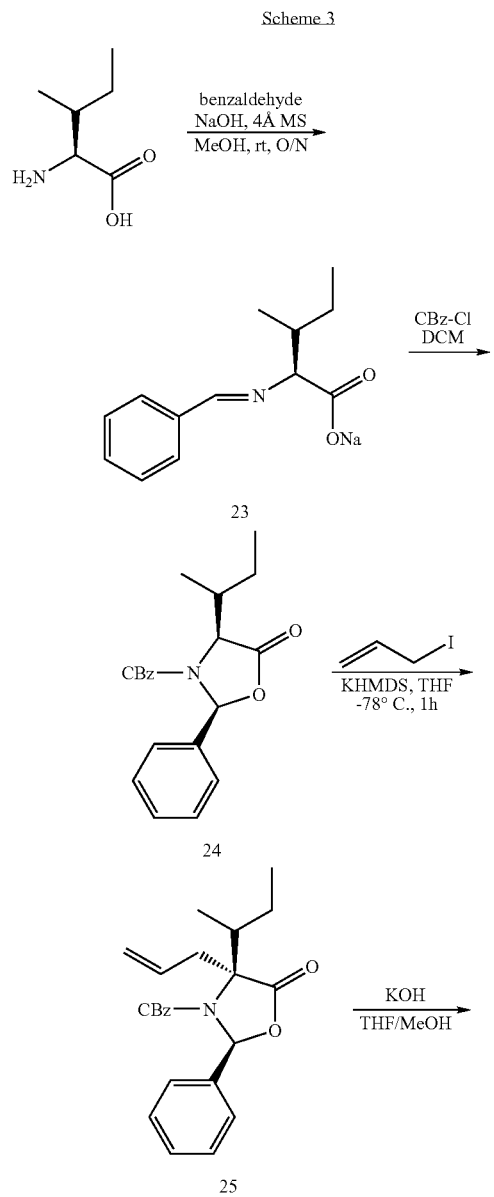

A quaternary amino acid, such as 26, may be coupled under standard conditions with glycine methyl ester using standard coupling reagents, like those previously described (Scheme 5). Oxidation of the allyl group in dipeptide 29 using ozonolysis or osmium tetroxide/sodium periodate provides the aldehyde 30 which is cyclized to the γ-lactam 31 using triethylsilane and trifluoroacetic acid (Holladay, M. W.; Nadzan, A. M. *J. Org. Chem.* 1991, 56, 3900-3905; Duan, J. PCT International Publication WO 0059285, 2000.

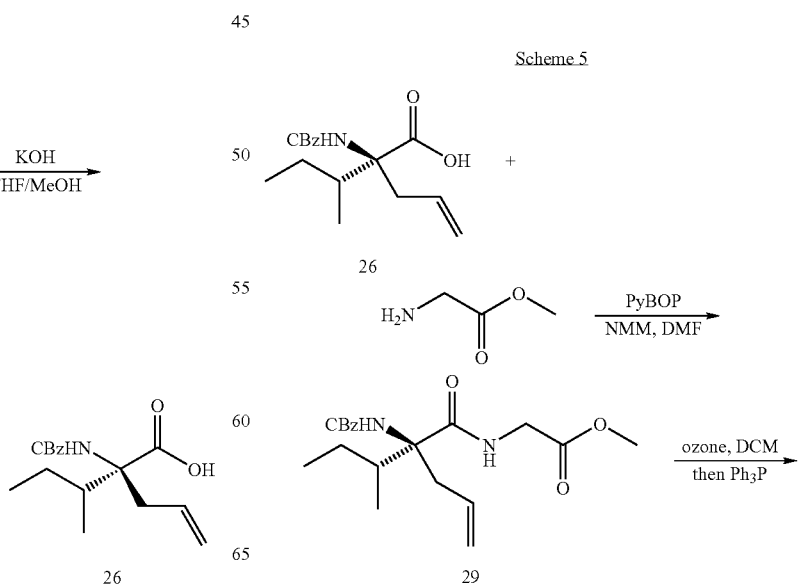

-continued

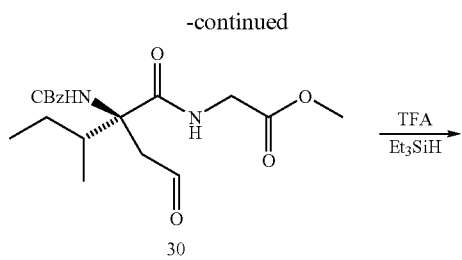

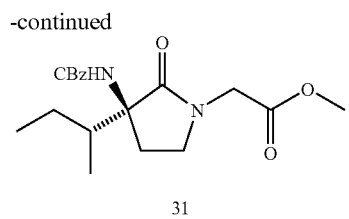

Lactams may also be synthesized in the manner demonstrated in Scheme 6, where the quaternary amino acid methyl ester, such as 32, is directly oxidized to the aldehyde 33, and glycine methyl ester is introduced by reductive alkylation using a reducing agent such as sodium borohydrode, sodium triacetoxyborohydride, or sodium cyanoborohydride to produce an amine 34. Intermediate 34 can be cyclized upon heating to form the desired γ-lactam 31 (see, for instance, Scheidt, K. A.; Roush, W. R.; McKerrow, J. H.; Selzer, P. M.; Hansell, E.; Rosenthal, P. J. *Bioorganic & Medicinal Chemistry* 1998, 6, 2477-2494.

The lactam amine protecting group (for example CBz) may now be removed by catalytic hydrogenation or other suitable methods to provide the free amine 36 (Scheme 7). The primary amine center may be further functionalized by reacting with agents such as carboxylic acids or their activated variants such as acid chlorides or acid anhydrides to make amides such as 37. Other derivatives of 37 can be prepared, including but not limited to the reaction with chloroformates to provide carbamates, or carbamoyl chlorides or isocyanates to provide ureas. The γ-lactams 37 can be deprotonated using a strong base, such as lithium bis(trimethylsilyl)amide, and alkylated with electrophiles, such as allyl bromide, 4-bromo-1-butene, or 3-bromo-2-methylpropene to afford products as mixtures of two diastereomers. The product diastereomers R-38 and S-38 can be separated using silica gel column chromatography or reverse phase HPLC. The corresponding γ-lactams acids S-4b can be obtained through basic hydrolysis of the esters S-38.

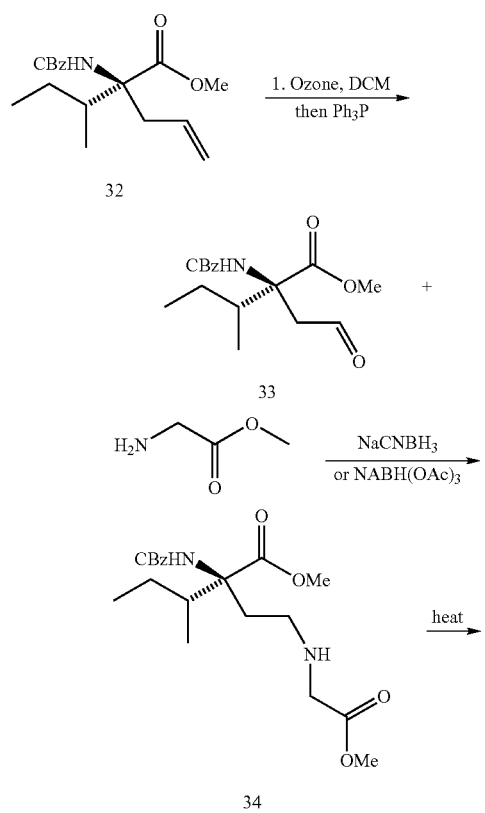

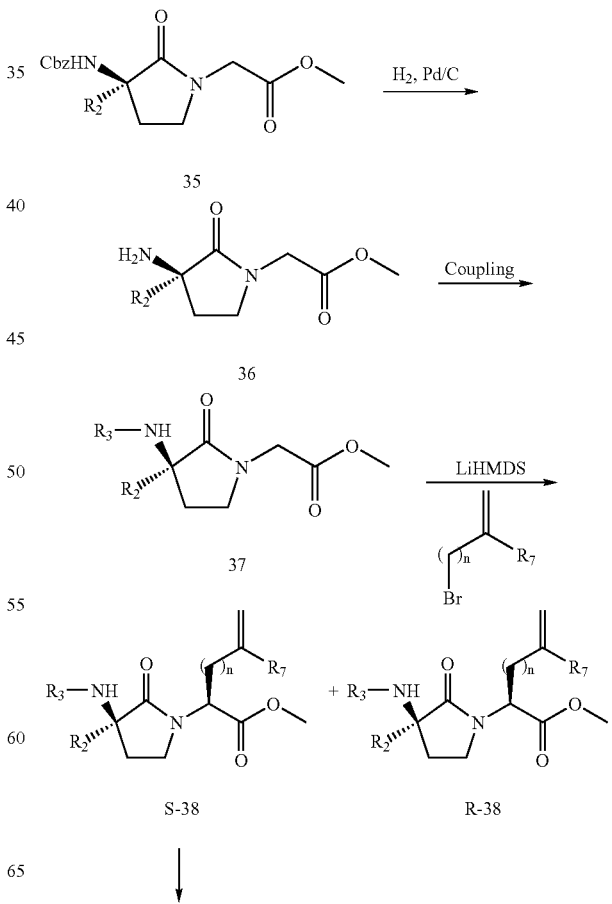

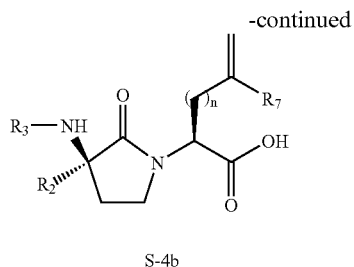

S-4b

A preferred subset of 2-hydroxy-1,3-diaminopropanes of formula 3 are represented by formula S-3a and are known as aminoindane allyl ethers. A

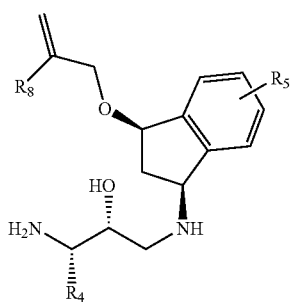

3a variety of N-protected aminoindan-1-ones 43 can be prepared from aryl aldehydes 39 using known literature methods (Scheme 8) (see, for instance, Dallemagne, P.; Pilo, J. C.; Rault, S.; Robba, M. *Bull. Chem. Soc. Fr.* 1993, 130, 121-124. Quermonne, M. A.; Dallemagne, P.; Louchahi-Raoul, J.; Pilo, J. C.; Rault, S.; Robba, M. *Eur. J. Med. Chem.* 1992, 27, 961-965.). Propionic acids 40 can be prepared from the condensation of aryl aldehydes 39 and malonic acid in the presence of ammonium formate. When $R_5$ is an electron donating group (i.e. methoxy), cyclization of propionic acids 40 to afford indanones 43 can be accomplished in a single step using trifluoroacetic anhydride and trifluoroacetic acid. In other cases (i.e. $R_5$=methyl or hydrogen), cyclization to indanones 43 can be performed using a three step protocol involving protection of the amino group as a trifluoroacetate, conversion of the carboxylic acid to an acid chloride, and Lewis-acid catalyzed cyclization. Reduction of the indanone 43 with borane.THF can provide a mixture of the cis- and trans-aminoindan-1-ols 44, favoring the cis diasteromer. Separation of the cis and trans diastereomers can be accomplished using silica gel column chromatography. Double deprotonation of alcohols 44, followed by alkylation with one equivalent of an electrophile, such as allyl bromide, allyl iodide, or 3-bromo-2-methylpropene, can provide the corresponding allyl ethers 45. Cleavage of the trifluoroacetate protecting group of intermediate 45 to afford aminoindane allyl ethers 46 can be accomplished using aqueous potassium carbonate in refluxing methanol. This method can be used to prepare either the cis- or trans-aminoindane allyl ethers 46 from cis- or trans-44, respectively.

Scheme 8

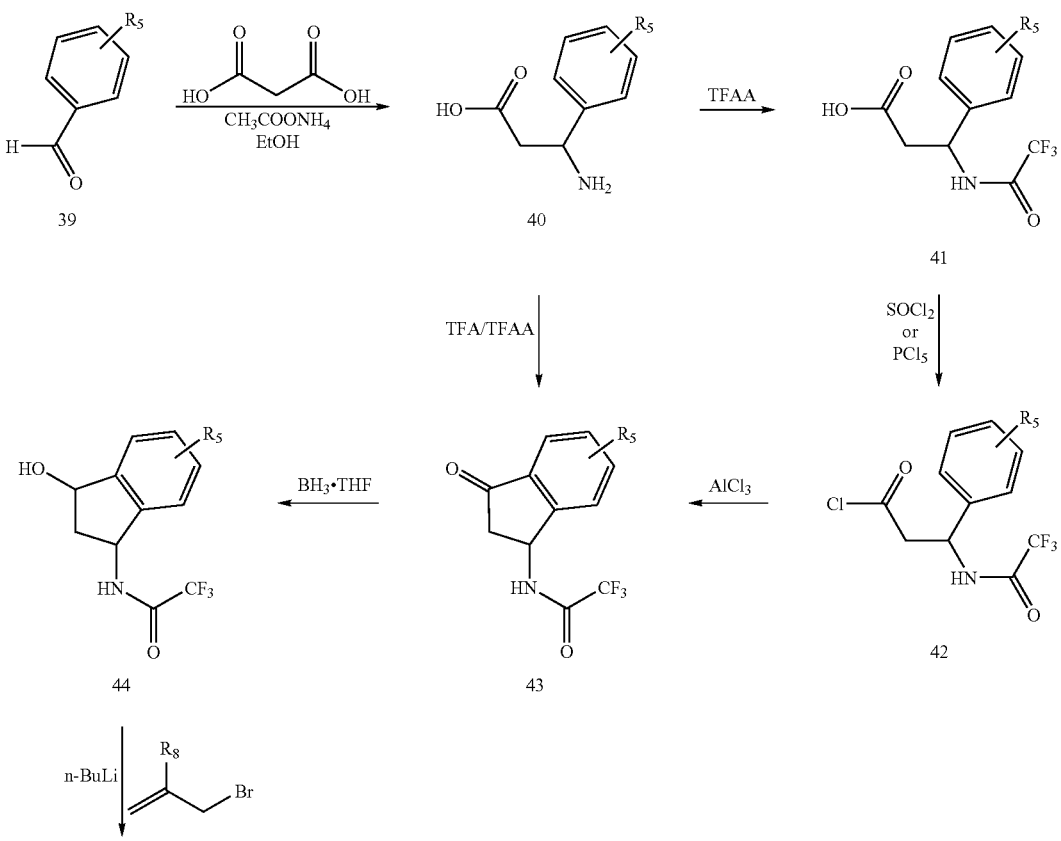

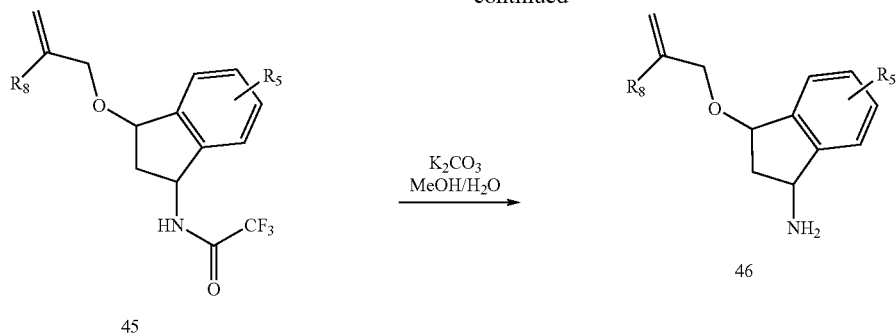

Enantiomerically enriched samples of cis- or trans-46 can be prepared from enantiomerically pure intermediates which may be obtained by chiral HPLC separation, selective crystallization of diastereomeric salts, or enzymatic resolution. For example, Saigo, K. et al. has described that both enantiomers of cis-3-aminoindan-1-ol can be obtained from its racemate using chiral HPLC separation methods, while both enantiomers of trans-3-aminoindan-1-ol may be obtained via chiral resolution of the racemate using (−)-dibenzoyl-L-tartaric acid as a resolving agent (Scheme 9) (Kinbara, K.; Katsumata, Y.; Saigo, K. *Chem. Letters* 2002, 266-267).

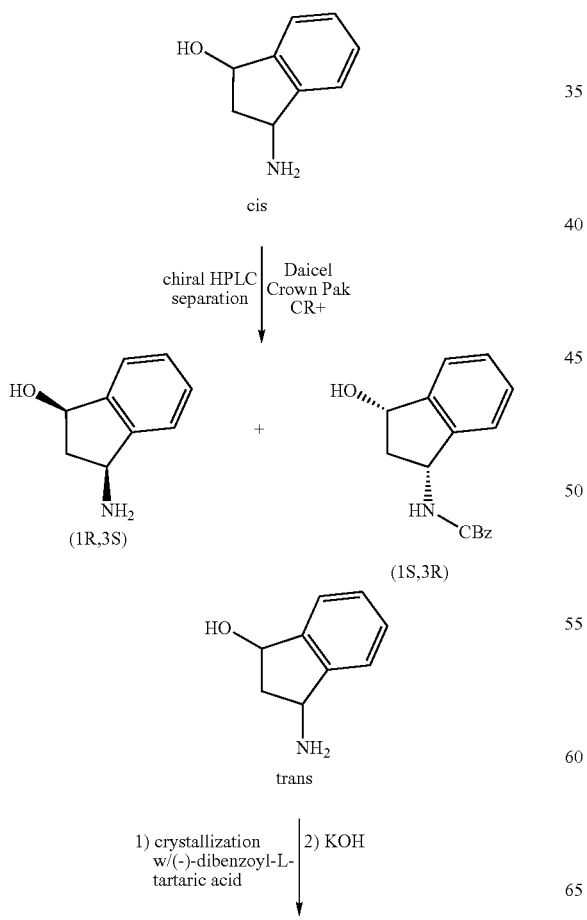

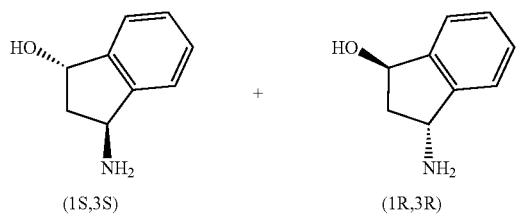

Additionally, Gotor, V. et al. has described a highly efficient biocatalytic resolution of benzyloxycarbonyl N-protected cis- and trans-3-aminoindan-1-ol using lipase B (CAL-B) isolated from *Candida Antarctica* (Scheme 9a) (Garcia-Lopez, M.; Alfonso, I.; Gotot, V. *Chem. Eur. J.* 2004, 10, 3006-3014).

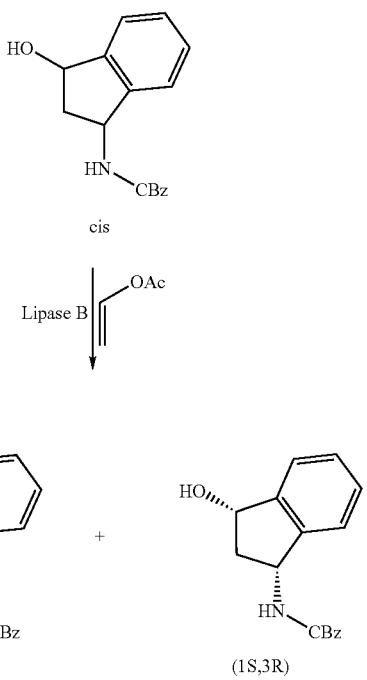

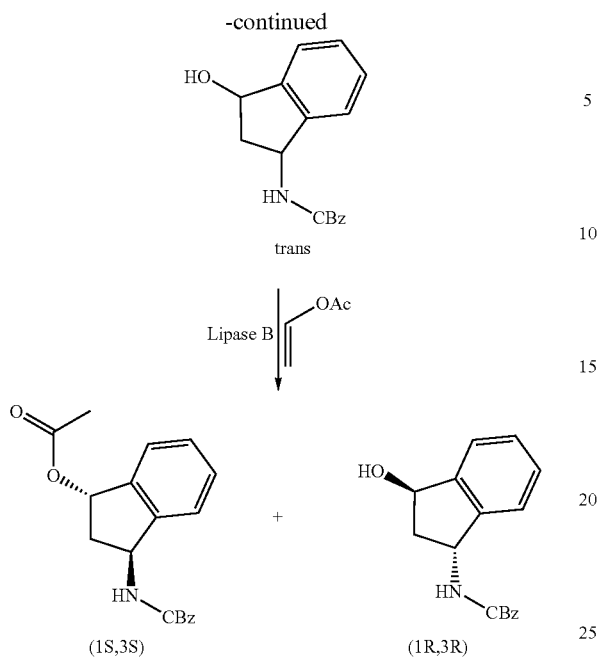

Scheme 10 discloses a method for preparing allyl-indane-1,3-diamines 52 from N-protected 3-aminoindan-1-ols 47. According to the method of Gotor, V. et al., Mitsunobu inversion of N-protected 3-aminoindan-1-ols 47 can provide the corresponding phthalimide, which after incubation with a methanolic solution of hydrazine affords the free amine 49 (Garcia-Lopez, M.; Alfonso, I.; Gotor, V. *Chem. Eur. J.* 2004, 10, 3006-3014). Alkylation of the amine with allyl bromide, allyl iodide, or 3-bromo-2-methylpropene, can provide the allyl amines 50. Tertiary amines 51 can be prepared from aldehydes and allyl amines 50 by using reductive alkylation methods known to one skilled in the art. Cleavage of the benzyloxycarbonyl protecting group under basic conditions, using barium hydroxide in refluxing 1,2-dimethoxyethane/water, can provide the corresponding allyl-indane-1,3-diamines 52.

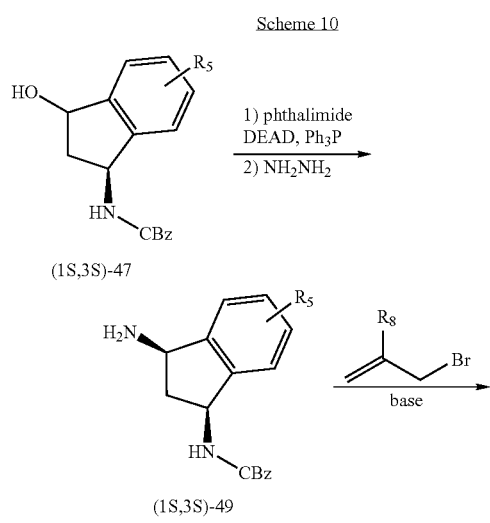

The synthesis of N-protected α-amino epoxides 13a is known to one skilled in the art and is disclosed in a number of references including, but not limited to those listed below. The starting materials for the process of preparing N-protected α-amino epoxides 13a are activated esters, represented by formula 53, wherein $R_4$ is as defined above and X is Cl or a phenyl ester substituted in the ortho or para position on the phenyl ring by hydrogen, halogen, or a nitro group (Scheme 11) (Kronenthal, D. et al., WO 02/14256 A1 and Decicco, C. P. et al. WO 2004/013098 A1.). The compounds represented by formula 53, are commercially available or can be prepared by techniques well known to those skilled in the art. The protecting group on the amino function is preferably Boc or CBz, but can also be other amino protecting groups which are recognized by those skilled in the art of organic synthesis.

In accordance with the present invention, an activated ester 53 is treated with a sulfur ylide to produce an intermediate keto ylide compound represented by 54. The sulfur ylide reagent is conveniently prepared from a sulfoxonium salt, such as trimethylsulfoxonium iodide, by reaction with a suitable base, such as sodium hydride, in an organic solvent. The keto-ylide compound 54 is then converted to the bromoketone 55 by reaction with a source of bromide, preferably lithium bromide, and an organic acid, such as methanesulfonic acid. The carbonyl group of the bromoketone 55 is then diastereoselectively reduced using a suitable hydride source such as borohydride or aluminum hydride, most preferably sodium borohydride, to afford an intermediate alcohol represented by formula 56, that spontaneously cyclizes to afford erythro epoxide 13a (Albeck, A.; Persky, R. *Tetrahedron* 1994, 50, 6333-6346.).

Scheme 11

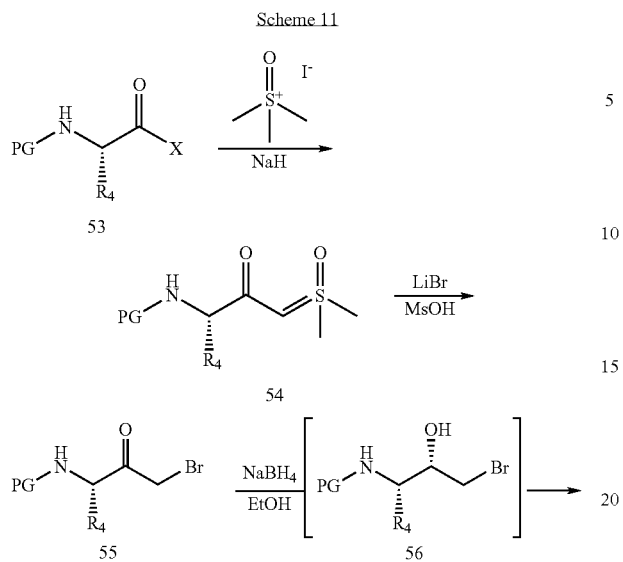

The epoxide 13a can be converted to the protected amino alcohol 57 by reaction with a primary amine 14, as previously defined, in a polar solvent such as tetrahydrofuran, acetonitrile, or alcohol, preferably acetonitrile. The reaction can be catalyzed with a Lewis-acid additive such as lithium-based salts, titanium-based salts, or aluminum-based salts, preferably lithium perchlorate. The reaction is carried out at a temperature range of 20-80° C. The amine protecting group of intermediate 57 can be removed using a variety of reagents and conditions to give amine 15. The reagents and conditions of choice for protecting group removal are dictated by the nature of the protecting group and are widely known to those skilled in the art. Barium hydroxide hydrate, in refluxing dimethoxyethane/water, is the preferred method when benzyloxycarbonyl (CBz) is used as the amine protecting group.

Scheme 12

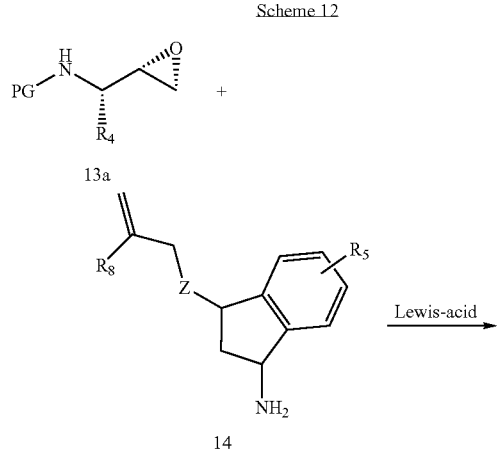

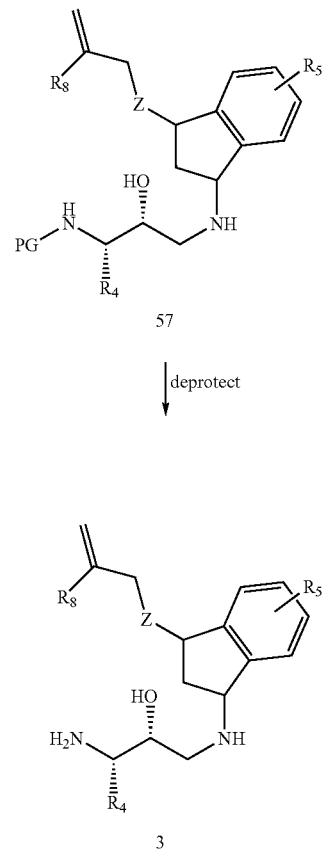

The coupling of lactam acid 4 with amino alcohol 3 using coupling methods previously described for the making amide bonds, such as EDC, HOBt, and DIEA in DMF, provides intermediate 2. The protonated salt of intermediate 2, such as trifluoroacetate or p-toluenesulfonate, can undergo ring closing metathesis to afford the unsaturated macrocycle Ib (for a comprehensive review of RCM chemistry see Trnka, T.; Grubbs, R. *Accounts of Chemical Research* 2001, 34, 18-29). The Grubbs Catalyst 2nd Generation A and the Hoveyda-Grubbs Catalyst B are preferable for promoting the RCM of protonated salts (i.e. hydrochloride, p-toluenesulfonic acid) of secondary amine containing substrates such as 2 (Furstner, A.; Grabowski, J.; Lehmann, C. W. *J. Org. Chem.* 1999, 64, 8275-8280. Wright, D. L.; Schulte, J. P.; Page, M. A. *Org. Lett.* 2000, 2, 1847-1850.). Additionally, the Hoveyda-Grubbs Catalyst may provide access to macrocycles possessing tri- and tetrasubstituted double bonds (Garber, S.; Kingsbury, J. S.; Gray, B.; Hoveyda, A. *J. Am. Chem. Soc.* 2000, 122, 8168-8179). Reduced macrocyclic diaminopropanes represented by formula Ia can be prepared by palladium catalyzed hydrogenation of the protonated salts, preferably trifluoroacetate salts, of unsaturated macrocycles Ib.

Scheme 13

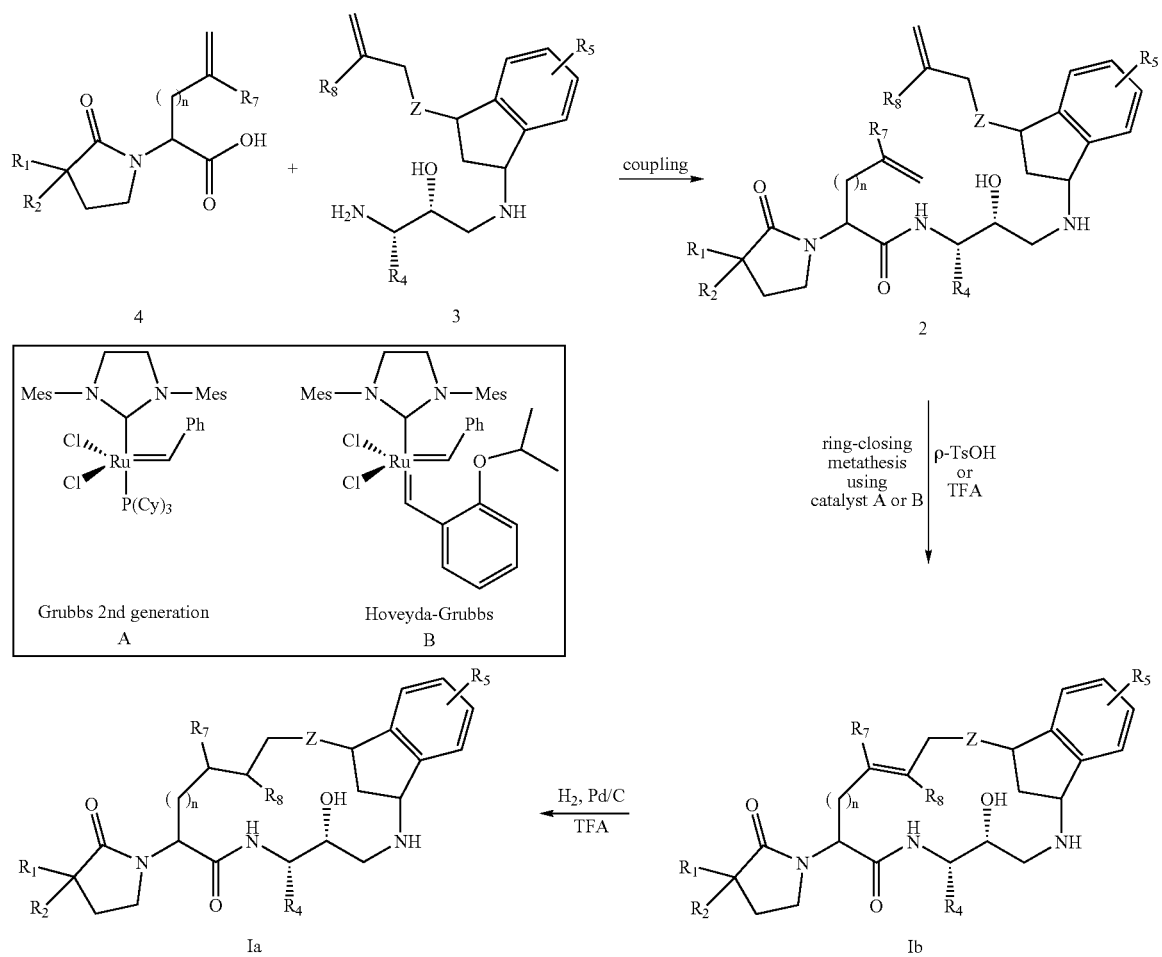

DESCRIPTION OF THE SPECIFIC EMBODIMENTS

The compounds of this application and their preparation can be understood further by the following working examples. These examples are meant to be illustrative of the present application, and are not to be taken as limiting thereof.

Chemical abbreviations used in the specification and Examples are defined as follows:
"Ac" for acetate,
"Boc" or "BOC" for t-butyloxycarbonyl,
"BOP" for benzotriazol-1-yloxytris-(dimethylamino)-phosphonium hexafluorophosphate,
"Cbz" for benzyloxycarbonyl,
"CDCl$_3$" for deuterochloroform,
"DCM" for dichloromethane,
"DIEA", "Hunig's base", or "DIPEA" for N,N-diisopropylethylamine,
"DME" for 1,2-dimethoxyethane,
"DMF" for N,N-dimethylformamide,
"DMAP" for 4-dimethylaminopyridine,
"DMSO" for dimethylsulfoxide,
"EDC" or "EDCI" for 1-(3-dimethylaminopropyl)-3-ethyl-carbodiimide hydrochloride,
"Et" for ethyl,
"EtOAc" for ethyl acetate,
"HOAc" for acetic acid,
"HOBt" for 1-hydroxybenzotriazole hydrate,
"HATU" for O-(7-azabenzotriazol-1-yl)-N,N,N',N'-tetramethyluronium hexafluorophosphate,
"LDA" for lithium diisopropylamide,
"LiHMDS" for lithium bis(trimethylsilyl)amide,
"n-BuLi" for n-butyllithium,
"NMM" for 4-methylmorpholine,
"PyBOP" for benzotriazole-1-yl-oxy-tris-pyrrolidino-phosphonium hexafluorophosphate,
"TBTU" for O-(1H-benzotriazol-1-yl)-N,N,N',N'-tetramethyluronium tetrafluoroborate,
"TEA" for triethylamine,
"TES" for triethylsilane,
"TFA" for trifluoroacetic acid, and
"THF" for tetrahydrofuran.

Abbreviations used in the Examples are defined as follows: "° C." for degrees Celsius, "MS" for mass spectrometry, "ESI" for electrospray ionization mass spectroscopy, "HR" for high resolution, "LC-MS" for liquid chromatography mass spectrometry, "eq" for equivalent or equivalents, "g" for gram or grams, "h" for hour or hours, "mg" for milligram or milligrams, "mL" for milliliter or milliliters, "mmol" for millimolar, "M" for molar, "min" for minute or minutes, "rt" for room temperature, "NMR" for nuclear magnetic resonance spectroscopy, "tlc" for thin layer chromatography, "atm" for atmosphere, and "α", "β", "R", "S", "E", and "Z" are stereochemical designations familiar to one skilled in the art.

"HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "standard conditions", samples were dissolved in methanol (1 mg/mL) and run using a gradient program with a solvent flow rate of 1.0 mL/min.

Reverse phase preparatory HPLC: When described as performed under "standard conditions", samples (approx. 20 mg) were dissolved in methanol (10 mg/mL) and purified on a 30 mm×100 mm Waters-Atlantis S5 column or a Phenomenex-Lune 30×100 mm 10 μm C18 column using a 10 minute gradient elution from 0% to 100% buffer B in buffer A (buffer A=10% MeOH/90% water/0.1% TFA and buffer B=90% MeOH/10% water/0.1% TFA).at 40 mL/minute.

Proton NMR spectra (referenced to tetramethylsilane) were obtained on a Bruker Avance 300, Avance 400, or Avance 500 spectrometer. Data were referred to the lock solvent. Electrospray Ionization (ESI) experiments were performed on a Micromass II Platform single-quadrupole mass spectrometer, or on a Finnigan SSQ7000 mass spectrometer.

The examples provided are intended to assist in a further understanding of the present disclosure. Particular materials employed, species and conditions are intended to further illustrate the specific embodiments of the invention and not limit the reasonable scope thereof.

SYNTHESIS OF INTERMEDIATES

Preparation A 2-(2-Oxopyrrolidin-1-yl)pent-4-enoic acid

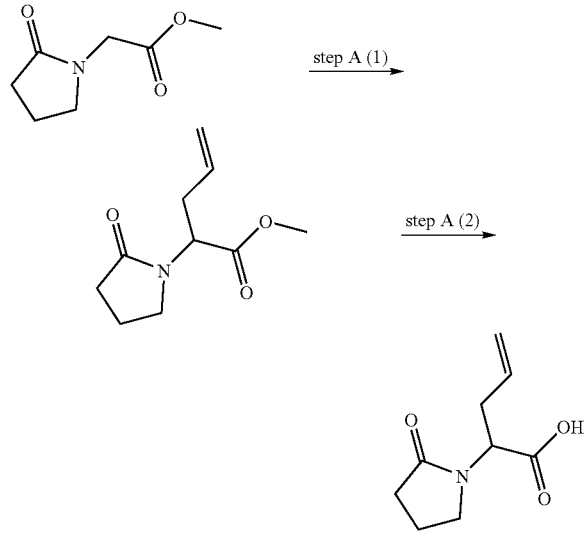

Step A(1): To a solution of the methyl 2-(2-oxopyrrolidin-1-yl)acetate (15 g, 95.5 mmol, TCI-America) in THF (600 mL) at −78° C. was added n-BuLi (42.0 mL, 105 mmol, 2.5 M in hexane, Aldrich). After 10 min, allyl bromide (9.7 mL, 115 mmol, Aldrich) was added. The mixture was stirred at −78° C. for 1 h and warmed to room temperature over 2 h. The reaction was then quenched with saturated ammonium chloride. After 15 min the mixture was extracted with EtOAc (3×200 mL). The combined organic layers were dried with $Na_2SO_4$ and concentrated in vacuo. The residue was purified by silica gel chromatography (20-80% EtOAc/hexanes linear gradient) to afford methyl 2-(2-oxopyrrolidin-1-yl)pent-4-enoate 4.0 g (21% yield) as pale yellow oil: LC-MS $(M+H)^+$=198.2; $^1$H NMR (400 MHz, $CDCl_3$) δ 5.67-5.69 (m, 1H), 5.04-5.14 (m, 2H), 4.88 (dd, J=10.70, 5.16 Hz, 1H), 3.70 (s, 3H), 3.44-3.69 (m, 1H), 3.34-3.37 (m, 1H), 2.68-2.75 (m, 1H), 2.36-2.46 (m, 3H), 1.94-2.07 (m, 2H).

Step A (2): A solution of LiOH (2 M, 0.73 g, 30.4 mmol) in 15 mL $H_2O$ was added to a solution of methyl 2-(2-oxopyrrolidin-1-yl)pent-4-enoate (2.0 g, 10.1 mmol) from step A(1) in THF (15 mL) at room temperature. The mixture was stirred at room temperature for 16 h. Poured into 1 N HCl. Extracted with EtOAc (3×250 mL). Washed combined organics with brine, dried with $Na_2SO_4$ After concentration in vacuo, dried on high-vacuum for ~3 h to give 1.5 g (81%) of 2-(2-oxopyrrolidin-1-yl)pent-4-enoic acid as a beige solid: LC-MS $(M+H)^+$=184.1; $^1$H NMR (300 MHz, $CDCl_3$) δ 11.85 (s, 1H), 5.47-5.81 (m, 1H), 4.91-5.25 (m, 2H), 4.81 (dd, J=11.14, 4.73 Hz, 1H), 3.45-3.59 (m, 1H), 3.25-3.40 (m, 1H), 2.59-2.83 (m, 1H), 2.30-2.52 (m, 3H), 1.80-2.12 (m, 2H).

Preparation B (S)-2-((S)-3-Butyl-2-oxopyrrolidin-1-yl)pent-4-enoic acid

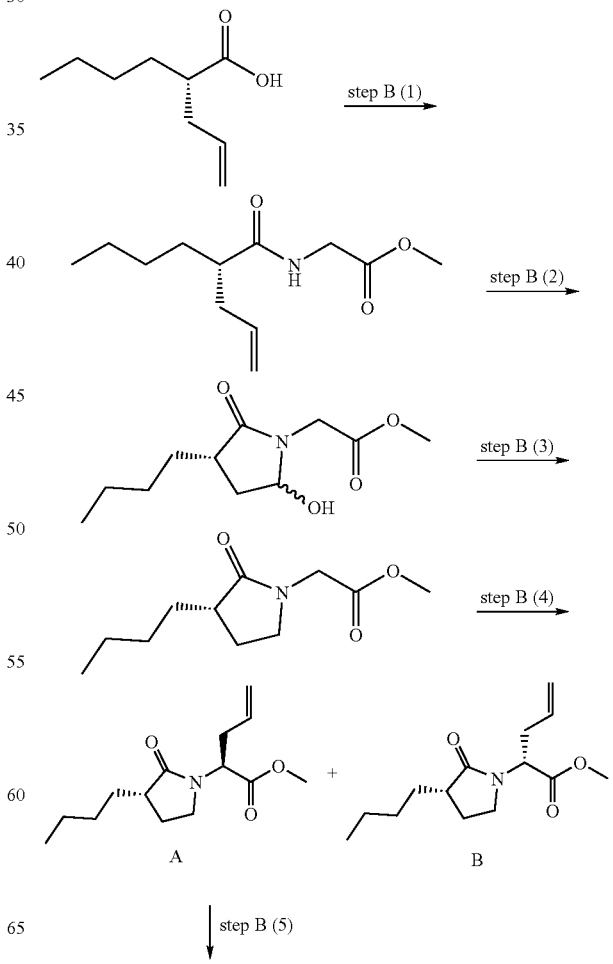

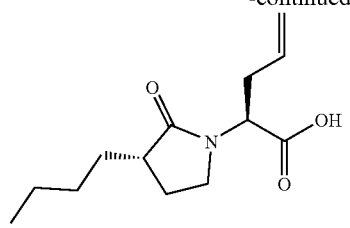

Step B (1): DIEA (1.35 mL, 9.9 mmol) was added to a mixture of (S)-2-allylhexanoic acid (300 mg, 1.92 mmol), methyl 2-aminoacetate hydrochloride (254 mg, 2.02 mmol), EDC (387 mg, 2.02 mmol), HOBt (273 mg, 2.02 mmol) in DMF (15 mL) at room temperature. The mixture was stirred for 18 h. Poured the reaction mixture into 200 mL 1 M HCl. Extracted with EtOAc/Hex (95:5) (2×200 mL). Washed combined organic extracts with brine, dried with $MgSO_4$, filtered and concentrated in vacuo. The residue was purified by silica gel chromatography (5-50% EtOAc/hexanes linear gradient) to give (S)-methyl 2-(2-allylhexanamido)acetate 360 mg (83% yield) as white solid: ESI $(M+H)^+$=228.2; $^1H$ NMR (500 MHz, $CDCl_3$) δ 5.90 (s, 1H), 5.64-5.85 (m, 1H), 4.95-5.14 (m, 2H), 4.04 (dd, J=5.04, 2.29 Hz, 2H), 3.75 (s, 3H), 2.28-2.46 (m, 1H), 2.07-2.29 (m, 2H), 1.62-1.64 (m, 1H), 1.46-1.47 (m, 1H), 1.18-1.36 (m, 4H), 0.87 (t, J=6.87 Hz, 3H).

Step B (2): A solution of $NaIO_4$ (10.7 g, 50.1 mmol) in 200 mL $H_2O$ was added portionwise over 10 min via pipette to a vigorously stirred solution of (S)-methyl 2-(2-allylhexanamido)acetate (3.8 g, 16.7 mmol) from step B (1) and 2 crystals of $OsO_4$ in 75 mL THF. After 16 h, poured the reaction mixture into the $H_2O$ (300 mL) and brine (100 mL). Extracted with EtOAc (2×300 ml). Washed the combined organics with brine (250 mL), dried over $Na_2SO_4$, filtered, and concentrated in vacuo. The crude product was used directly in step B (3).

Step B (3): TFA (30 mL) was added to the mixture of the alcohol from step B (2) and TES (13.3 mL, 83.5 mmol) in $CH_2Cl_2$ (150 mL) at 0° C. Removed cold bath and stirred for 2 h. The solution was concentrated in vacuo. The residue was purified by silica gel chromatography (5-45% EtOAc/hexanes linear gradient) to give (S)-methyl 2-(3-butyl-2-oxopyrrolidin-1-yl)acetate 2.0 g (56% yield) as colorless oil: LC-MS $(M+H)^+$=214.2; $^1H$ NMR (300 MHz, $CDCl_3$) δ 3.93-4.18 (m, 2H), 3.70 (s, 3H), 3.27-3.46 (m, 2H), 2.31-2.53 (m, 1H), 2.12-2.31 (m, 1H), 1.77-1.94 (m, 1H), 1.63-1.80 (m, 1H), 1.20-1.47 (m, 5H), 0.78-0.99 (m, 3H).

Step B (4): (S)-Methyl 2-(3-butyl-2-oxopyrrolidin-1-yl)acetate (0.5 g, 2.35 mmol) from step B (3) was dissolved in dry THF (30 mL) and cooled to −78° C. Lithium bis(trimethylsilyl)amide (1.0M in THF, 2.70 mL, 2.70 mmol, Aldrich) was added while the temperature was maintained below −60° C. The mixture was cooled to −78° C. and stirred for 15 min. A solution of allyl bromide (0.24 mL, 2.72 mmol, Aldrich) in 10 mL of THF was added dropwise and the resulting mixture was stirred for 48 h. The reaction was quenched with acetic acid (0.5 mL) and poured into 75 mL of 0.5 M $H_2SO_4$. The aqueous layer was extracted with EtOAc and the organic layers were concentrated in vacuo. The residue was purified by silica gel chromatography (5-35% EtOAc/hexanes linear gradient) to give 170 mg (29% yield) of (s)-methyl 2-((S)-3-butyl-2-oxopyrrolidin-1-yl)pent-4-enoate (diastereomer A, first to elute) as a colorless oil and 130 mg of (R)-methyl 2-((S)-3-butyl-2-oxopy-rrolidin-1-yl)pent-4-enoate (diastereomer B, second to elute) as a colorless oil. Data for diastereomer A: LC-MS $(M+H)^+$=254.3; $^1H$ NMR (500 MHz, $CDCl_3$) δ 5.47-5.95 (m, 1H), 4.98-5.20 (m, 2H), 4.87 (dd, J=10.99, 4.88 Hz, 1H), 3.69 (s, 3H), 3.32-3.51 (m, 1H), 3.15-3.34 (m, 1H), 2.60-2.80 (m, 1H), 2.41-2.53 (m, 1H), 2.26-2.40 (m, 1H), 2.05-2.23 (m, 1H), 1.76-1.94 (m, 1H), 1.61-1.77 (m, 1H), 1.18-1.47 (m, 5H), 0.78-0.97 (m, 3H). Data for diastereomer B: LC-MS $(M+H)^+$=254.36; $^1H$ NMR (500 MHz, $CDCl_3$) δ 5.57-5.78 (m, 1H), 4.99-5.18 (m, 2H), 4.88 (dd, J=10.99, 4.88 Hz, 1H), 3.69 (s, 3H), 3.32-3.48 (m, 1H), 3.21-3.32 (m, 1H), 2.64-2.79 (m, 1H), 2.34-2.53 (m, 2H), 2.10-2.30 (m, 1H), 1.74-1.91 (m, 1H), 1.46-1.74 (m, 1H), 1.20-1.40 (m, 5H), 0.78-1.00 (m, 3H).

Step B (5): A solution of LiOH (2 M, 69 mg, 2.9 mmol) in 1.4 mL of $H_2O$ was added to diastereomer A, (S)-methyl 2-((S)-3-butyl-2-oxopyrrolidin-1-yl)pent-4-enoate, (242 mg, 0.96 mmol) from Step B (4) in THF (1.4 mL). The reaction mixture was stirred at room temperature for 3 days. The mixture was poured into 1 N HCl and the aqueous layer was extracted with EtOAc. The combined organic layers were washed with brine, dried over $NaSO_4$ and concentrated in vacuo to give 182 mg of (S)-2-((S)-3-butyl-2-oxopyrrolidin-1-yl)pent-4-enoic acid as colorless oil: LC-MS $(M+H)^+$=240.2; $^1H$ NMR (500 MHz, $CDCl_3$) δ 5.60-5.82 (m, 1H), 5.03-5.21 (m, 2H), 4.74 (dd, J=10.68, 4.88 Hz, 1H), 3.38-3.48 (m, 1H), 3.29-3.38 (m, 1H), 2.70-2.81 (m, 1H), 2.51-2.62 (m, 1H), 2.36-2.49 (m, 1H), 2.11-2.25 (m, 1H), 1.79-1.91 (m, 1H), 1.66-1.79 (m, 1H), 1.23-1.43 (m, 5H), 0.80-0.96 (m, 3H).

Preparation C cis-3-(Allyloxy)-6-methoxy-2,3-dihydro-1H-inden-1-amine

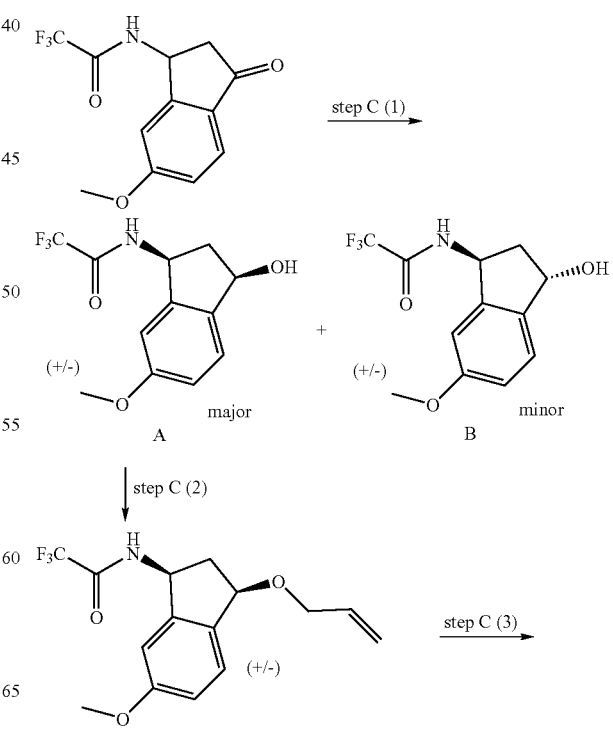

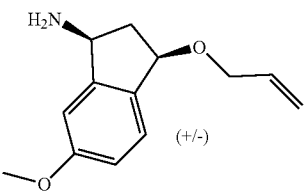

Step C (1): BH$_3$.THF (1.0 M, 44 mL, 43.8 mmol) was added to a solution of 2,2,2-trifluoro-N-(6-methoxy-3-oxo-2,3-dihydro-1H-inden-1-yl)acetamide (6.0 mg, 21.9 mmol) [Dallemagne, P.; Pilo, J. C.; Rault, S.; Robba, R. M. *Bull. Soc. Chim. Fr.* 1993, 130, 121-124] in THF at −20° C. The reaction mixture was warmed to room temperature and stirred overnight. Carefully quenched with MeOH. Poured the mixture into H$_2$O and extracted with EtOAc. Washed with brine, dried over MgSO$_4$, filtered, and concentrated in vacuo. The residue was purified by silica gel chromatography (33-75% EtOAc/hexanes linear gradient) to give 4.49 g (74% yield) of cis-2,2,2-trifluoro-N-3-hydroxy-6-methoxy-2,3-dihydro-1H-inden-1-yl)acetamide (diastereomers A, first to elute) as a white solid and 1.29 g (21% yield) of trans-2,2,2-trifluoro-N-3-hydroxy-6-methoxy-2,3-dihydro-1H-inden-1-yl)acetamide (diastereomers B, second to elute) as a white solid. Both diastereomers were independently recrystallized from EtOAc/Hex to provide 4.0 g (66% yield) of diastereomer A and 1.0 g (17% yield) of diasteromer B as white crystalline solids. Data for cis-2,2,2-trifluoro-N-3-hydroxy-6-methoxy-2,3-dihydro-1H-inden-1-yl)acetamide (diastereomers A): LC-MS (M+Na)$^+$=298.1; $^1$H NMR (500 MHz, DMSO-d$_6$) δ 9.79 (d, J=8.24 Hz, 1H), 7.29 (d, J=8.24 Hz, 1H), 6.78-7.06 (m, 1H), 6.66 (s, 1H), 5.44 (d, J=5.80 Hz, 1H), 5.14-5.16 (m, 1H), 4.92-4.96 (m, 1H), 3.74 (s, 3H), 2.67-2.83 (m, 1H), 1.73-1.91 (m, 1H). Data for trans-2,2,2-trifluoro-N-3-hydroxy-6-methoxy-2,3-dihydro-1H-inden-1-yl)acetamide (diastereomers B): $^1$H NMR (500 MHz, DMSO-d$_6$) δ 9.71 (d, J=7.94 Hz, 1H), 7.29 (d, J=8.24 Hz, 1H), 6.90 (dd, J=8.39, 1.98 Hz, 1H), 6.74 (d, J=2.14 Hz, 1H), 5.38-5.58 (m, 1H), 5.11-5.13 (m, 2H), 3.74 (s, 3H), 2.13-2.37 (m, 2H).

Step C (2): A solution of cis-2,2,2-trifluoro-N-3-hydroxy-6-methoxy-2,3-dihydro-1H-inden-1-yl)acetamide (1.81 g, 6.58 mmol) diastereomers A from stepC(1) in 40 mL of THF was cooled to −78° C. Added n-BuLi (4.07 mL, 10.2 mmol, 2.5M in hexanes, Aldrich). Allowed the precipitous mixture to stir at −78° C. for 30 min. Added allyl bromide (0.440 mL, 5.09 mmol, Aldrich) and warmed to room temperature. The reaction mixture became homogeneous. Stirred at room temperature for 3 days. Quenched with 1 M HCl. Extracted with EtOAc. Washed the combined organics with brine, dried over Na$_2$SO$_4$, filtered and concentrated in vacuo. The residue was purified by silica gel chromatography (10-60% EtOAc/hexanes linear gradient) to provide 811 mg (39% yield) of cis-N-(3-(allyloxy)-6-methoxy-2,3-dihydro-1H-inden-1-yl)-2,2,2-trifluoroacetamide as a white solid. The solid was recrystallized from EtOAc/Hex to afford 445 mg (21% yield) of analytically pure material: HR-MS (M+NH$_4$)$^+$=333.1423; $^1$H NMR (500 MHz, CDCl$_3$) δ 7.33 (d, J=8.24 Hz, 1H), 6.94 (d, J=2.14 Hz, 1H), 6.89 (dd, J=8.55, 2.44 Hz, 2H), 5.85-5.95 (m, 1H), 5.35-5.42 (m, 1H), 5.29 (d, J=1.83 Hz, 1H), 5.19 (dd, J=10.38, 1.53 Hz, 1H), 4.79 (dd, J=5.49, 2.14 Hz, 1H), 4.01-4.10 (m, 2H), 3.80 (s, 3H), 2.63-2.70 (m, 1H), 2.05-2.12 (m, 1H); Anal. calcd. for C$_{15}$H$_{16}$F$_3$NO$_3$: C, 57.14; H, 5.12; O 15.22. Found: C, 57.27; H, 5.11; O, 4.39.

Step C (3): cis-N-(3-(Allyloxy)-6-methoxy-2,3-dihydro-1H-inden-1-yl)-2,2,2-trifluoroacetamide (650 mg, 2.06 mmol) from stepC (2), potassium carbonate (1.42 g, 10.3 mmol) and MeOH (70 mL)/H$_2$O (4.4 mL) were heated at reflux for 7 h. The reaction mixture was concentrated in vacuo. Added water to the residue, extracted with EtOAc, washed the organic layers with brine, dried over Na$_2$SO$_4$, filtered and concentrated in vacuo to afford 450 mg (99% yield) of cis-3-(allyloxy)-6-methoxy-2,3-dihydro-1H-inden-1-amine as a light brown oil: LC-MS (M+H)$^+$=220.2; $^1$H NMR (500 MHz, DMSO-d$_6$) δ 7.19 (d, J=8.24 Hz, 1H), 6.97 (d, J=2.14 Hz, 1H), 6.78 (dd, J=8.24, 2.44 Hz, 1H), 5.81-6.07 (m, 1H), 5.30 (dd, J=17.09, 1.83 Hz, 1H), 5.15 (dd, J=10.53, 1.68 Hz, 1H), 4.72 (t, J=6.87 Hz, 1H), 4.02-4.21 (m, 2H), 3.96 (t, J=7.48 Hz, 1H), 3.73 (s, 3H), 2.64-2.88 (m, 1H), 1.39-1.58 (m, 1H).

Preparation D

Diastereomeric mixture of:

(2R,3S)-1-((1S,3R)-3-(Allyloxy)-6-methoxy-2,3-dihydro-1H-inden-1-ylamino)-3-amino-4-phenylbutan-2-ol and (2R,3S)-1-((1R,3S)-3-(Allyloxy)-6-methoxy-2,3-dihydro-1H-inden-1-ylamino)-3-amino-4-phenylbutan-2-ol

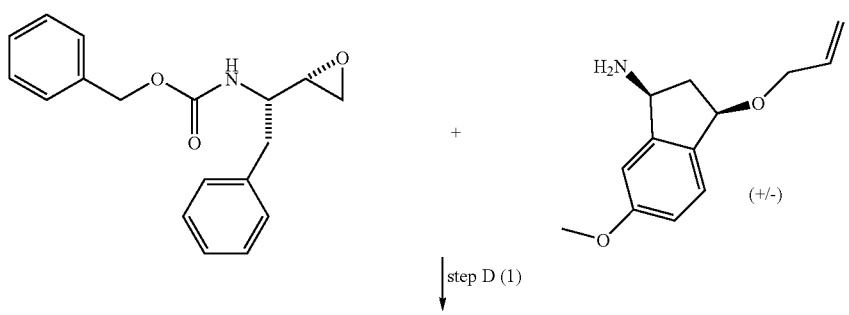

step D (1)

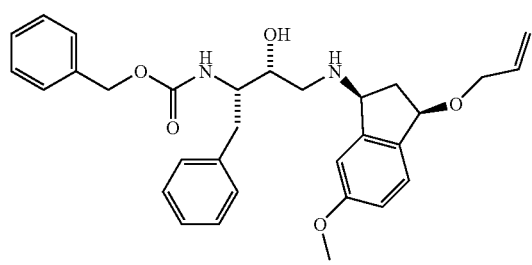 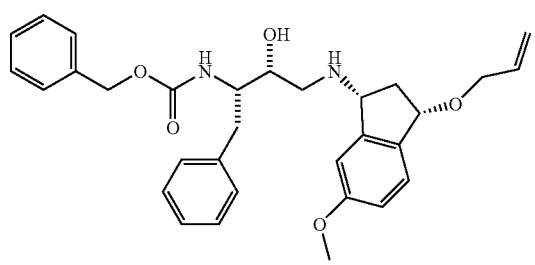

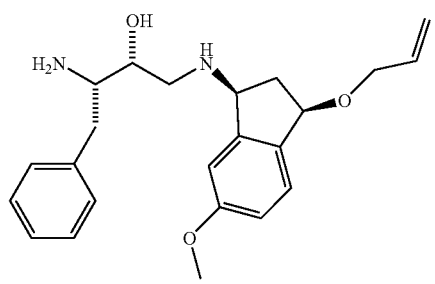 + 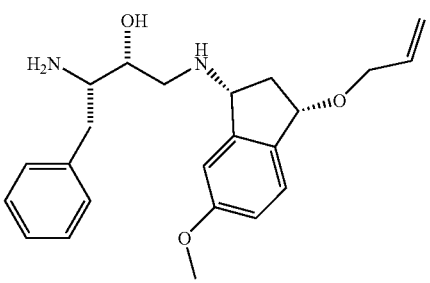

step D (2)

Step D (1): A mixture of benzyl (S)-1-((S)-oxiran-2-yl)-2-phenylethylcarbamate (862 mg, 2.90 mmol), (1S,3R)-3-(allyloxy)-6-methoxy-2,3-dihydro-1H-inden-1-amine (451 mg, 2.06 mmol) in CH$_3$CN (10 mL) with LiClO$_4$ (657 mg, 6.17 mmol) was stirred at 30° C. for 2.5 days. Poured the reaction mixture into brine/NaHCO$_3$ solution and extracted with EtOAc. The combined organics were washed with brine, dried over Na$_2$SO$_4$, filtered and concentrated in vacuo. The residue was purified by silica gel chromatography (1-20% MeOH (containing 0.1% triethylamine)/chloroform linear gradient) to give 931 mg (88% yield) of the desired mixture of diastereomers: LC-MS (M+H)$^+$=517.3; $^1$H NMR (500 MHz, CDCl$_3$) δ 7.05-7.43 (m, 12H), 6.70-6.97 (m, 2H), 5.79-6.10 (m, 1H), 5.22-5.39 (m, 1H), 5.17 (d, J=10.38 Hz, 1H), 4.94-5.10 (m, 2H), 4.00-4.14 (m, 3H), 3.83-3.95 (m, 1H), 3.75-3.80 (m, 3H), 3.49-3.55 (m, 1H), 3.48 (s, 2H), 2.80-3.05 (m, 3H), 2.72 (dd, J=12.05, 6.87 Hz, 1H), 2.57-2.68 (m, 1H), 1.83-1.93 (m, 1H).

Step D (2): A mixture of the products from stepD(1) (235 mg, 0.455 mmol), Ba(OH)$_2$.H$_2$O (235 mg, 1.37 mmol), DME/H$_2$O (3 mL/2 mL) was heated at 110° C. in a sealed tube. After 24 h, the mixture was cooled to room temperature and filtered through a short pad of Celite. The reaction vessel and filtercake was rinsed with fresh DME. The filtrate was concentrated in vacuo. The crude product was purified using reverse phase preparatory HPLC. The fractions containing product were neutralized with solid NaHCO$_3$ prior to concentration in vacuo. Water was added to the solid residue, the aqueous mixture was extracted with EtOAc, the organic layers were dried over Na$_2$SO$_4$, filtered and concentrated in vacuo to provide 70 mg (40% yield) of the title diastereomers as a clear viscous residue: LC-MS (M+H)$^+$=383.1 $^1$H NMR (500 MHz, DMSO-d$_6$) δ 7.11-7.34 (m, 6H), 6.94 (dd, J=5.34, 2.29 Hz, 1H), 6.83 (dd, J=8.24, 2.14 Hz, 1H), 5.85-6.05 (m, 1H), 5.23-5.42 (m, 1H), 5.14 (dd, J=10.53, 1.68 Hz, 1H), 4.75 (q, J=5.90 Hz, 1H), 4.01-4.16 (m, 2H), 3.99 (d, J=3.05 Hz, 1H), 3.74 (s, 3H), 3.39 (dd, J=6.26, 4.73 Hz, 1H), 2.84-2.98 (m, 1H), 2.58-2.84 (m, 2H), 2.18-2.46 (m, 2H), 1.50-1.82 (m, 1H).

Preparation E (2R,3S)-1-((1S,3R)-3-(Allyloxy)-6-methoxy-2,3-dihydro-1H-inden-1-ylamino)-3-amino-4-(3,5-difluorophenyl)butan-2-ol

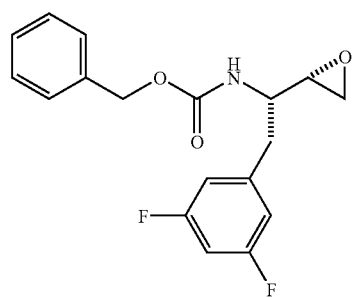 + 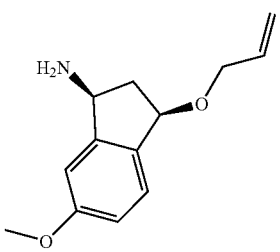

step E (1)

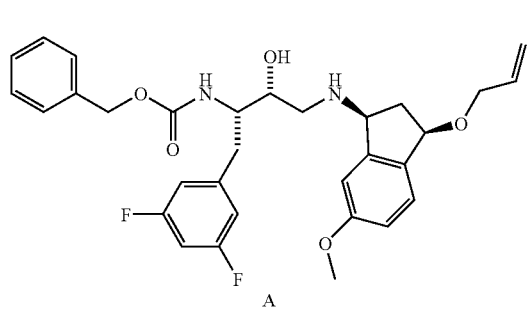

A

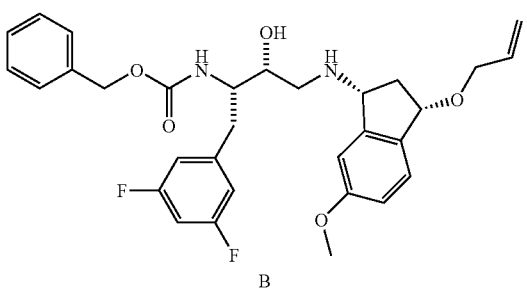

B

↓ step E (2)

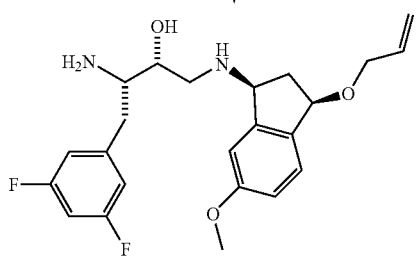

Step E (1): A mixture of benzyl (S)-2-(3,5-difluorophenyl)-1-((S)-oxiran-2-yl)ethylcarbamate (1.0 g, 3.0 mmol), cis-3-(allyloxy)-6-methoxy-2,3-dihydro-1H-inden-1-amine (657 mg, 3.0 mmol) and LiClO$_4$ (1.60 g, 15 mmol) in CH$_3$CN (10 mL) with was stirred at 30° C. for 2.5 days. The resulting mixture was poured into brine/NaHCO$_3$ solution and extracted with EtOAc. The combined organic layers were washed with brine, dried over Na$_2$SO$_4$, filtered and concentrated in vacuo. The residue was purified by silica gel chromatography (1-20% MeOH (containing 0.1% triethylamine)/chloroform linear gradient) to give two pure diastereomers 265 mg (16% yield) of benzyl (2S,3R)-4-((1S,3R)-3-(allyloxy)-6-methoxy-2,3-dihydro-1H-inden-1-ylamino)-1-(3,5-difluorophenyl)-3-hydroxybutan-2-ylcarbamate (diastereomer A, first to elute) and 270 mg (16% yield) of benzyl (2S,3R)-4-((1R,3S)-3-(allyloxy)-6-methoxy-2,3-dihydro-1H-inden-1-ylamino)-1-(3,5-difluorophenyl)-3-hydroxybutan-2-ylcarbamate (diastereomer B, second to elute). Data for diastereomer A: HRMS (M+H)$^+$= 553.2534; $^1$H NMR (500 MHz, DMSO-d$_6$) δ 7.21-7.35 (m, 4H), 7.14-7.21 (m, 2 H), 7.03 (t, J=9.46 Hz, 1H), 6.87-6.99 (m, 3H), 6.83 (dd, J=8.24, 2.14 Hz, 1H), 5.88-6.00 (m, 1H), 5.30 (dd, J=17.09, 1.83 Hz, 1H), 5.14 (dd, J=10.53, 1.98 Hz, 1H), 4.96-5.02 (m, 1H), 4.83-4.95 (m, 2H), 4.75 (t, J=6.41 Hz, 1H), 4.01-4.13 (m, 2H), 3.91-4.00 (m, 1H), 3.72-3.76 (m, 3H), 3.64-3.72 (m, 1H), 3.44-3.53 (m, 1H), 3.06 (dd, J=13.73, 3.05 Hz, 1H), 2.65-2.75 (m, 1H), 2.54-2.65 (m, 2H), 1.92-2.02 (m, 1H), 1.57-1.67 (m, 1H). Data for diastereomer B: HRMS (M+H)$^+$=553.2509; $^1$H NMR (500 MHz, DMSO-d$_6$) δ 7.20-7.37 (m, 4H), 7.12-7.22 (m, 2H), 6.98-7.13 (m, 1H), 6.86-7.00 (m, 3H), 6.82 (dd, J=8.24, 2.14 Hz, 1H), 5.80-6.05 (m, 1H), 5.30 (dd, J=17.40, 1.83 Hz, 1H), 5.14 (d, J=10.38 Hz, 1H), 4.80-5.03 (m, 3H), 4.74 (t, J=5.95 Hz, 1H), 3.99-4.15 (m, 2H), 3.95 (t, J=6.10 Hz, 1H), 3.62-3.77 (m, 3H), 3.49 (d, J=4.88 Hz, 1H), 3.03 (dd, J=13.89, 3.20 Hz, 1H), 2.54-2.80 (m, 4H), 2.01-2.18 (m, 1H), 1.59-1.76 (m, 1H).

Step E (2): Ba(OH)$_2$.H$_2$O (267 mg, 1.41 mmol) was added to a vial charged with benzyl (2S,3R)-4-((1S,3R)-3-(allyloxy)-6-methoxy-2,3-dihydro-1H-inden-1-ylamino)-1-(3,5-difluorophenyl)-3-hydroxybutan-2-ylcarbamate (diastereomer A, 260 mg, 0.471 mmol) from stepE(1), DME/H$_2$O (3 mL/2 mL). The sealed vial was heated at 110° C. for 18 h. Filtered the reaction mixture through a Pasture pipette/Kimwipe plug to remove solids. Rinsed the vessel and solids with fresh DME. The filtrate was evaporated in vacuo. Residual solvents were removed under high vacuum. The crude residue was purified by silica gel chromatography (1-20% MeOH (containing 0.1% triethylamine)/chloroform linear gradient) to give 74 mg (38% yield) the of the title compound as a clear viscous oil. LC-MS (M+H)$^+$=419.24; $^1$H NMR (500 MHz, CDCl$_3$) δ 7.32 (d, J=8.24 Hz, 1H), 6.92 (d, J=2.14 Hz, 1H), 6.85 (dd, J=8.24, 2.44 Hz, 1H), 6.71-6.80 (m, 2H), 6.60-6.71 (m, 1H), 5.84-6.03 (m, 1H), 5.30 (dd, J=17.24, 1.68 Hz, 1H), 5.18 (dd, J=10.38, 1.53 Hz, 1H), 4.77 (dd, J=6.10, 3.97 Hz, 1H), 4.08-4.12 (m, 2H), 4.05 (dd, J=6.87, 4.43 Hz, 1H), 3.79 (s, 3H), 3.47-3.52 (m, 1H), 3.04-3.10 (m, 1H), 2.90-3.00 (m, 2H), 2.75 (dd, J=11.90, 8.55 Hz, 1H), 2.61-2.68 (m, 1H), 2.49 (dd, J=13.43, 9.77 Hz, 1H), 1.94-2.00 (m, 1H).

Preparation L (S)-2-((S)-3-Acetamido-3-sec-butyl-2-oxopyrrolidin-1-yl)pent-4-enoic acid

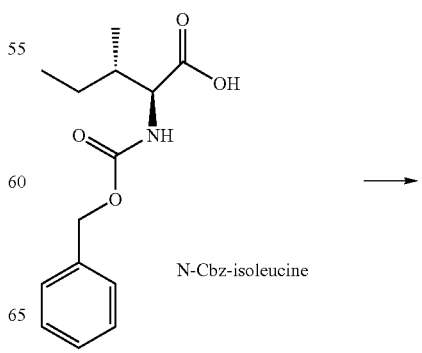

N-Cbz-isoleucine

→

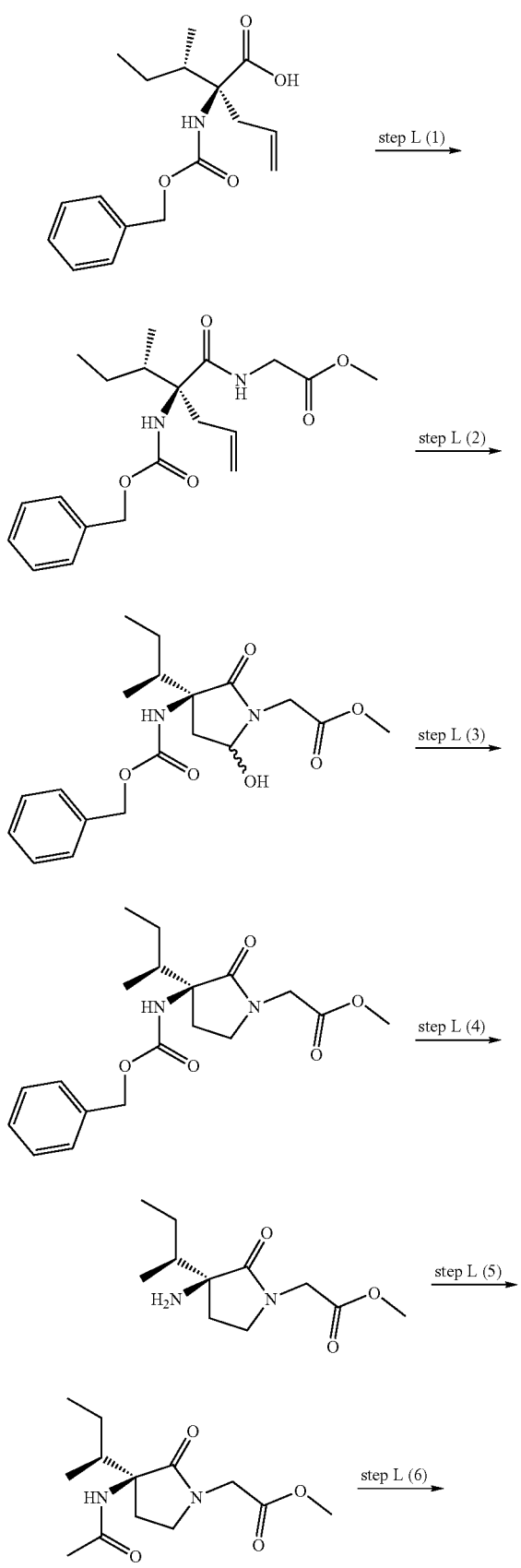

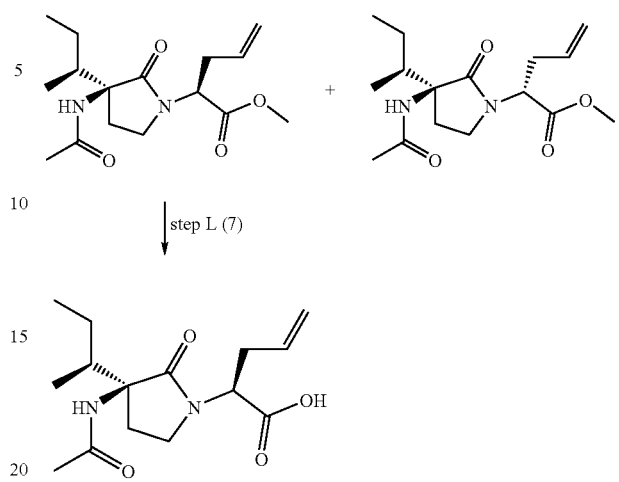

Step L (1): NMM (9.8 mL, 89.1 mmol) was added to a mixture of methyl 2-aminoacetate hydrochloride (3.95 g, 31.4 mmol), (2S)-2-(benzyloxycarbonyl-amino)-2-sec-butylpent-4-enoic acid (8.0 g, 26.2 mmol) [prepared as described in WO 2004/013098] HATU (12 g, 31.4 mmol in DCM (300 mL) at room temperature. The mixture was stirred for 16 h. Poured the reaction mixture into 150 mL $H_2O$. Extracted with DCM (3×250 mL). Washed combined organic extracts with brine, dried with $Na_2SO_4$, filtered and concentrated in vacuo. The residue was purified by silica gel chromatography to give methyl 2-((2S)-2-(benzyloxycarbonylamino)-2-sec-butylpent-4-enamido)acetate 9.8 g (99% yield) as a yellow-oily residue: ESI (M+H)$^+$=377.43. $^1$H NMR (300 MHz, CDCl$_3$) δ ppm 0.93-1.08 (m, 6H) 1.49-1.56 (m, 3H) 2.74-2.89 (m, 2H) 3.68 (s, 3H) 4.10-3.96 (m, 2H) 5.00-5.22 (m, 4H) 5.85-5.94 (m, 1H) 7.33-7.40 (m, 5H).

Step L (2): A solution of NaIO$_4$ (16.7 g, 78 mmol) in $H_2O$ was added over 10 min. period via pipette to a vigorously stirred solution of 2-((2S)-2-(benzyloxycarbonylamino)-2-sec-butylpent-4-enamido)acetate (9.8 g, 26.0 mmol) from step L (1) and 2 crystals of OsO$_4$ in 120 mL of THF. Followed the reaction by LC-MS. After 16 h, poured the reaction into $H_2O$ (300 mL) and brine (100 mL). Extracted with EtOAC (2×300 ml). Washed the combined organics with brine (250 mL), dried over $Na_2SO_4$, filtered, and concentrated in vacuo. The crude product was used as is in the next step.

Step L (3): TFA (100 mL) was added to the mixture of the alcohol from step L (2) and TES (20.8 mL, 130 mmol) in $CH_2Cl_2$ (300 mL) at 0° C. Removed cold bath and stirred for 2 h. The reaction was shown to go to completion by LC-MS. The solution was concentrated in vacuo and used as is in the next step. The reaction afforded methyl 2-((S)-3-(benzyloxycarbonylamino)-3-sec-butyl-2-oxopyrrolidin-1-yl)acetate 6.69 g (68%) as colorless oil. LC-MS (M+H)$^+$=363.39. $^1$H NMR (300 MHz, CDCl$_3$) δ ppm 0.80-1.13 (m, 7H) 1.52-1.85 (m, 2H) 2.18-2.48 (m, 2H) 3.43 (s, 2H) 3.69 (s, 4H) 4.52 (d, J=17.93 Hz, 1H) 5.01 (q, J=12.08 Hz, 2H) 5.22 (s, 1H) 7.25-7.39 (m, 5H).

Step L (4): 10% Pd/C (1.0 g) was added to a round-bottom flask charged with a solution of the methyl ester (1.2 g, 3.37 mmol) from step L (3) in MeOH (50 mL) under $N_2$. Evacuated and flushed with $H_2$. Stirred the mixture under $H_2$ balloon overnight. Filtered through Celite and concentrated the filtrate to afford 860 mg of the title compound. The crude product was used as is in the next step. LC-MS $(M+H)^+=$ 229.20.

Step L (5): Suspended the free amine from step L (4) in DCM (40 mL). To this solution was added 2 N NaOH (4.0 mL) and acetyl chloride (0.60 mL). Stirred vigorously for 6 h. The reaction was shown to go to completion by LC-MS. Diluted with DCM and $H_2O$. Extracted DCM (3×200 mL). Combined organic layers, washed with brine, dried over $Na_2SO_4$, and concentrated in vacuo. Afforded 788 mg (77% yield) of methyl 2-((S)-3-acetamido-3-sec-butyl-2-oxopyrrolidin-1-yl)acetate as an off-white residue: LC-MS $(M+H)^+=271.32$. $^1H$ NMR (300 MHz, $CDCl_3$) δ ppm 0.81-1.18 (m, 7H) 1.52-1.66 (m, 1H) 1.77-1.87 (m, 1H) 1.89-1.97 (m, 3H) 2.21-2.49 (m, 2H) 3.35-3.51 (m, 2H) 3.62-3.76 (m, 4H) 4.48 (d, J=17.57 Hz, 1H) 5.86 (s, 1H).

Step L (6): Methyl 2-((S)-3-acetamido-3-sec-butyl-2-oxopyrrolidin-1-yl)acetate (0.5 g, 1.85 mmol) from step L (5) was dissolved in dry THF (30 mL) and cooled to −78° C. Lithium bis(trimethylsilylamide (11.0M in THF, 3.70 mL, 3.70 mmol, Aldrich) was added while the temperature was maintained below −60° C. The mixture was cooled to −78° C. and stirred for 15 min. A solution of allyl bromide (3.13 mL, 37 mmol, Aldrich) in 10 mL of THF was added drop wise and the resulting mixture was stirred for 5 days. The reaction was followed by TLC (1:1 EtOAC/Hex) and LC-MS. The reaction was quenched with acetic acid (0.5 mL) and poured into 75 mL of 0.5M $H_2SO_4$. The aqueous layer was extracted with EtOAC and concentrated organic layers in vacuo. The residue was purified by chiral chromatography to give two pure diastereomers: (R)-methyl 2-((S)-3-acetamido-3-sec-butyl-2-oxopyrrolidin-1-yl)pent-4-enoate (diastereomer A, 77 mg, yellow solid), LC-MS $(M+H)^+=311.03$. $^1H$ NMR (300 MHz, $CDCl_3$) δ ppm 0.81-1.08 (m, 7H) 1.73-1.86 (m, 1H) 1.94 (s, 3H) 2.34-2.53 (m, 3H) 2.65-2.79 (m, 1H) 3.18-3.30 (m, 1H) 3.42-3.55 (m, 1H) 3.66-3.76 (m, 3H) 4.77 (dd, J=10.61, 5.12 Hz, 1H) 4.99-5.19 (m, 2H) 5.58-5.75 (m, 1H) 5.88 (s, 1H); (S)-methyl 2-((S)-3-acetamido-3-sec-butyl-2-oxopyrrolidin-1-yl)pent-4-enoate (diastereomer B, 122 mg, white waxy solid): LC-MS $(M+H)^+$ =311.03. $^1H$ NMR (300 MHz, $CDCl_3$) δ ppm 0.86-1.13 (m, 7H) 1.77-1.86 (m, 1H) 1.94 (s, 3H) 2.26-2.38 (m, 2H) 2.53 (dd, J=9.70, 6.77 Hz, 1H) 2.65-2.79 (m, 1H) 3.27-3.37 (m, 1H) 3.41-3.53 (m, 1H) 3.64-3.72 (m, 3H) 4.87 (dd, J=9.51, 5.86 Hz, 1H) 5.04-5.20 (m, 2H) 5.68-5.86 (m, 2H).

Step L (7): A solution of $LiOH/H_2O$ (2M, 28 mg in 0.50 mL) was added to the diastereomer B, (S)-methyl 2-((S)-3-acetamido-3-sec-butyl-2-oxopyrrolidin-1-yl)pent-4-enoate (122 mg, 0.39 mmol) from Step L (6) in THF (1.0 mL) at RT. The reaction was stirred for 3 days. The mixture was poured into 1N HCl and the aqueous layer was extracted with EtOAC. The combined organic layers were washed with brine, dried over $NaSO_4$ and concentrated in vacuo to give 102 mg of the title compound as white solid. LC-MS $(M+H)^+=297.01$.

Preparation M (S)-2-((S)-3-isobutyl-2-oxopyrrolidin-1-yl)pent-4-enoic acid

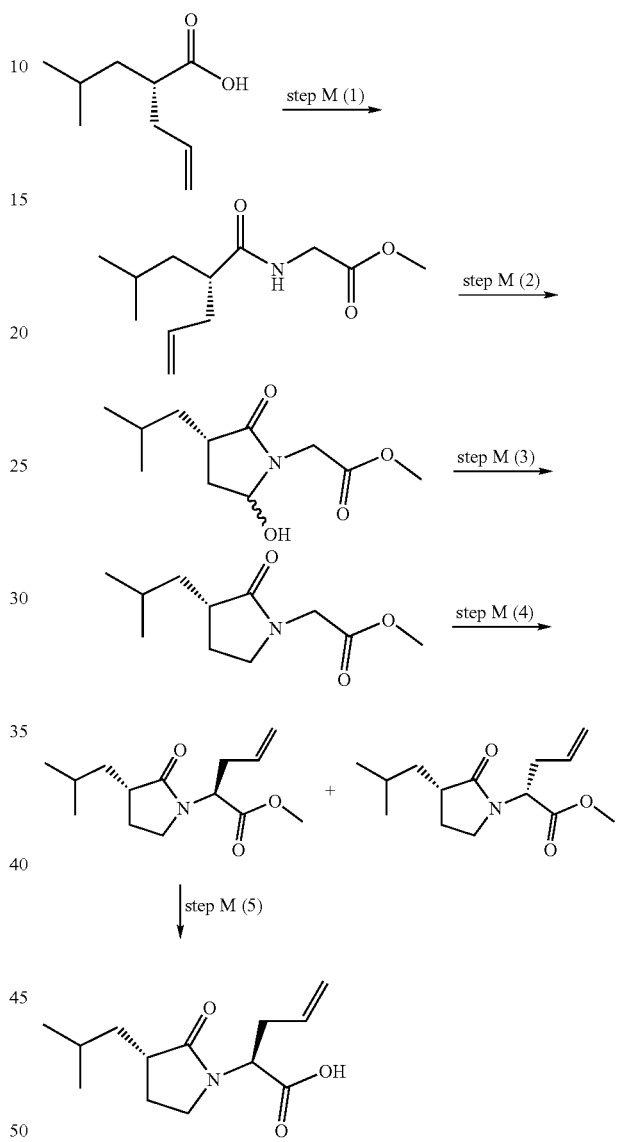

Step M (1): NMM (11.0 mL, 100 mmol) was added to a mixture of methyl 2-aminoacetate hydrochloride (4.44 g, 35.3 mmol), (S)-2-isobutylpent-4-enoic acid [prepared as described in WO 2004/013098] (4.6 g, 29.5 mmol), HATU (13.4 g, 35.3 mmol in DCM (200 mL) at room temperature. The mixture was stirred for 16 h. Poured the reaction mixture into 150 mL $H_2O$. Extracted with DCM (3×250 mL). Washed combined organic extracts with brine, dried with $Na_2SO_4$, filtered and concentrated in vacuo. The residue was purified by silica gel chromatography to give (S)-methyl 2-(2-isobutylpent-4-enamido)acetate 4.0 g (60% yield) as a colorless oil: ESI $(M+H)^+=228.22$. $^1H$ NMR (300 MHz, $CDCl_3$) δ ppm 0.79-0.93 (m, 6H) 1.15-1.30 (m, 1H)

1.48-1.71 (m, 2H) 2.08-2.38 (m, 3H) 3.72 (s, 3H) 4.01 (d, J=5.12 Hz, 2H) 4.92-5.09 (m, 2H) 5.63-5.78 (m, 1H) 5.92 (s, 1H).

Step M (2): A solution of NaIO$_4$ (11.3 g, 52.8 mmol) in H$_2$O was added over 10 min. period via pipette a vigorously stirred solution of (S)-methyl 2-(2-isobutylpent-4-enamido) acetate (4.0 g, 17.6 mmol) from step M (1) and 2 crystals of OsO$_4$ in 100 mL of THF. Followed the reaction by LC-MS. After 16 h, poured the reaction into the H$_2$O (300 mL) and brine (100 mL). Extracted with EtOAC (2×300 ml). Washed the combined organics with brine (250 mL), dried over Na$_2$SO$_4$, filtered, and concentrated in vacuo. The crude product was used as is in the next step.

Step M (3): TFA (60 mL) was added to the mixture of the alcohol from step M (2) and TES (13.4 mL, 87 mmol) in CH$_2$Cl$_2$ (200 mL) at 0° C. Removed cold bath and stirred for 2 h. The mixture was shown to go to completion by LC-MS. The solution was concentrated in vacuo and used as is in the next step. The reaction afforded (S)-methyl 2-(3-isobutyl-2-oxopyrrolidin-1-yl)acetate 2.5 g (63%) as colorless oil: LC-MS (M+H)$^+$=214.18. $^1$H NMR (300 MHz, CDCl$_3$) δ ppm 0.83-0.95 (m, 6H) 1.16-1.30 (m, 1H) 1.59-1.77 (m, 3H) 2.14-2.29 (m, 1H) 2.41-2.57 (m, 1H) 3.29-3.46 (m, 2H) 3.69 (s, 3H) 3.94-4.17 (m, 2H).

Step M (4): (S)-methyl 2-(3-isobutyl-2-oxopyrrolidin-1-yl)acetate (500 mg, 2.35 mmol) from step M (3) was dissolved in dry THF (30 mL) and cooled to −78° C. Lithium bis(trimethylsilylamide (1.0M in THF, 2.70 mL, 2.70 mmol, Aldrich) was added while the temperature was maintained below −60° C. The mixture was cooled to −78° C. and stirred for 15 min. A solution of allyl bromide (0.23 mL, 2.73 mmol, Aldrich) in 10 mL of THF was added drop wise and the resulting mixture was stirred for 5 days. The reaction was followed by TLC (1:1 EtOAC/Hex) and LC-MS. The reaction was quenched with acetic acid (0.5 mL) and poured into 75 mL of 0.5M H$_2$SO$_4$. The aqueous layer was extracted with EtOAC and concentrated organic layers in vacuo. The residue was purified by silica-gel chromatography to give two pure diastereomers: (S)-methyl 2-((S)-3-isobutyl-2-oxopyrrolidin-1-yl)pent-4-enoate (diastereomer A, 138 mg), LC-MS (M+H)$^+$=254.26. $^1$H NMR (300 MHz, CDCl$_3$) δ ppm 0.80-0.95 (m, 6H) 1.15-1.29 (m, 1H) 1.55-1.76 (m, 3H) 2.06-2.22 (m, 1H) 2.31-2.52 (m, 2H) 2.61-2.78 (m, 1H) 3.17-3.28 (m, 1H) 3.34-3.48 (m, 1H) 3.67 (s, 3H) 4.87 (dd, J=10.80, 4.94 Hz, 1H) 5.00-5.14 (m, 2H) 5.57-5.77 (m, 1H); (R)-methyl 2-((S)-3-isobutyl-2-oxopyrrolidin-1-yl)pent-4-enoate (diastereomer B, 60 mg), LC-MS (M+H)$^+$=254.23. $^1$H NMR (300 MHz, CDCl$_3$) δ ppm 0.82-0.95 (m, 6H) 1.11-1.26 (m, 1H) 1.45-1.78 (m, 3H) 2.11-2.25 (m, 1H) 2.35-2.50 (m, 2H) 2.63-2.78 (m, 1H) 3.20-3.43 (m, 2H) 3.64-3.72 (m, 3H) 4.86 (dd, J=10.98, 5.12 Hz, 1H) 5.00-5.15 (m, 2H) 5.55-5.77 (m, 1H).

Step M (5): A solution of LiOH/H$_2$O (2M, 40 mg in 1.0 mL) was added to the diastereomer A, (S)-methyl 2-((S)-3-isobutyl-2-oxopyrrolidin-1-yl)pent-4-enoate (138 mg, 0.55 mmol) from Step M (4) in THF (1.0 mL) at RT. The reaction was stirred for 3 days. The mixture was poured into 1N HCl and the aqueous layer was extracted with EtOAC. The combined organic layers were washed with brine, dried over NaSO4 and concentrated in vacuo to give 88 mg (67%) of the title compound as white solid: LC-MS (M+H)$^+$=240.04. $^1$H NMR (300 MHz, CDCl$_3$) δ ppm 0.82-0.95 (m, 7H) 1.16-1.30 (m, 1H) 1.59-1.79 (m, 3H) 2.09-2.26 (m, 1H) 2.39-2.60 (m, 2H) 2.68-2.80 (m, 1H) 3.24-3.48 (m, 2H) 4.67-4.76 (m, 1H) 5.01-5.20 (m, 2H) 5.60-5.79 (m, 1H).

EXAMPLE 1

(4R,5S)-5-Benzyl-4-hydroxy-18-methoxy-8-(2-oxo-pyrrolidin-1-yl)-13-oxa-2,6-diaza-tricyclo [12.6.1.0$^{15,20}$]henicosa-10,15(20),16,18-tetraen-7-one

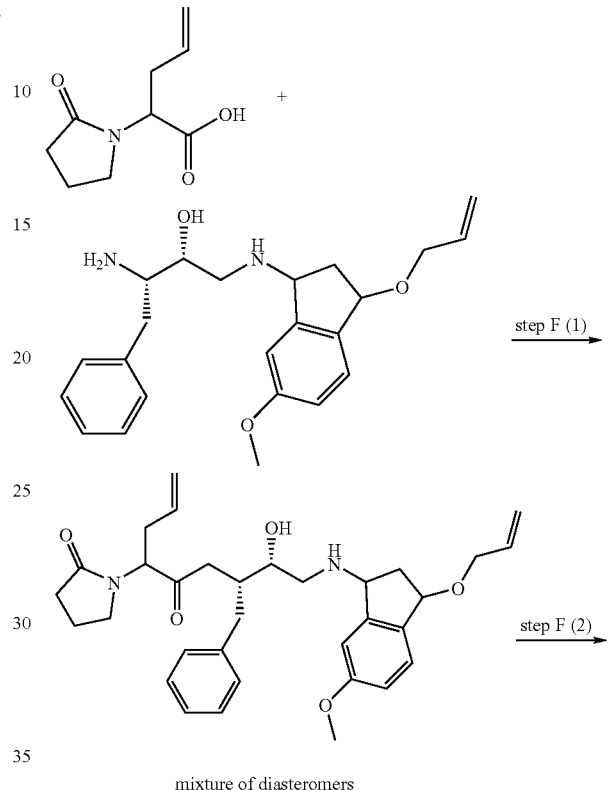

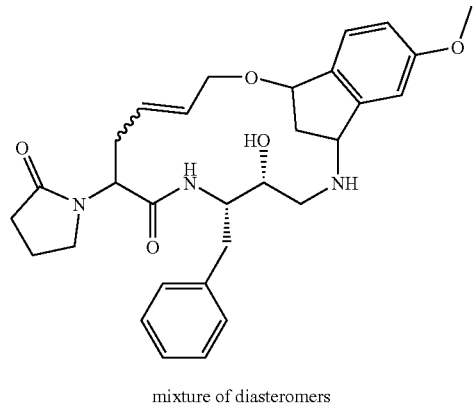

mixture of diastereomers

Step F (1): The diastereomer mixture of products (70 mg, 0.183 mmol) from stepD(2), 2-(2-oxopyrrolidin-1-yl)pent-4-enoic acid (35 mg, 0.192 mmol) from stepA(2), EDC (37 mg, 0,192 mmol), HOBt (26 mg, 0.192 mmol), DIEA (0.163 mL, 0.915 mmol) were mixed in 4 mL of DMF. The mixture was stirred at room temperature for 18 h. The crude product was purified using reverse phase preparatory HPLC. The fractions containing product were neutralized with solid NaHCO$_3$ prior to concentration in vacuo. Water was added to the solid residue, the aqueous mixture was extracted with EtOAc, the organic layers were dried over Na$_2$SO$_4$, filtered and concentrated in vacuo to provide 69 mg of N-((2S,3R)-4-(3-(allyloxy)-6-methoxy-2,3-dihydro-1H-inden-1-ylamino)-3-hydroxy-1-phenylbutan-2-yl)-2-(2-oxopyrroli-din-1-yl)pent-4-enamide as a mixture of several diastereomers: LC-MS (M+H)$^+$=548.7; HRMS (M+H)$^+$=

548.3101; ¹H NMR (500 MHz, CDCl₃) δ 7.09-7.38 (m, 7H), 6.76-7.01 (m, 2H), 5.85-6.04 (m, 1H), 5.39-5.70 (m, 1H), 5.24-5.39 (m, 1H), 5.18 (d, J=10.38 Hz, 1H), 4.91-5.13 (m, 2H), 4.66-4.88 (m, 1H), 3.99-4.59 (m, 5H), 3.70-3.91 (m, 3H), 3.41-3.58 (m, 1H), 2.92-3.34 (m, 2H), 2.53-2.97 (m, 5H), 2.40-2.55 (m, 1H), 2.11-2.42 (m, 3H), 1.92-2.13 (m, 1H), 1.53-2.01 (m, 4H).

Step F (2): p-Toluenesulfonic acid monohydrate (33.2 mg, 0.175 mmol) was added to a solution of the diastereomers from stepF(1) (96 mg, 0.175 mmol) in CH₂Cl₂ (20 mL). The heterogeneous mixture was stirred for 20 min at room temperature under dry N₂, resulting in a slightly turbid solution Grubbs 2$^{nd}$ generation catalyst [(1,3-bis-(2,4,6-tri-methylphenyl)-2-imidazolidinylidene)-dichloro(phenylm-ethylene)(tricyclohexylphosphine)ruthenium] (30 mg, 0.035 mmol, Aldrich) was added and the resulting mixture stirred under N₂ for 18 h at room temperature. The reaction mixture was evaporated to dryness, passed through pipet silica gel plug eluting with 5% MeOH/CDCl₃. The eluent was evaporated to dryness. The crude product was purified using reverse phase preparatory HPLC. The fractions containing product were neutralized with solid NaHCO₃ prior to concentration in vacuo. Water was added to the solid residue, the aqueous mixture was extracted with EtOAc, the organic layers were dried over Na₂SO₄, filtered and concentrated in vacuo to provide 89 mg (97% yield) of the title compound as a mixture of several diastereomers: LC-MS (M+H)⁺= 520.6; HRMS (M+H)⁺=520.2806; ¹H NMR (500 MHz, DMSO-d₆) δ 6.79-8.12 (m, 8H), 5.20-5.98 (m, 2H), 4.62-5.01 (m, 2H), 4.08-4.55 (m, 2H), 3.84-4.10 (m, 3H), 3.61-3.86 (m, 3H), 2.55-3.59 (m, 3H), 1.92-2.43 (m, 4H), 1.38-2.01 (m, 4H), 0.68-1.52 (m, 3H).

EXAMPLE 2

(4R,5S)-5-Benzyl-4-hydroxy-18-methoxy-8-(2-oxo-pyrrolidin-1-yl)-13-oxa-2,6-diaza-tricyclo[12.6.1.0$^{15,20}$]henicosa-15(20),16,18-trien-7-one

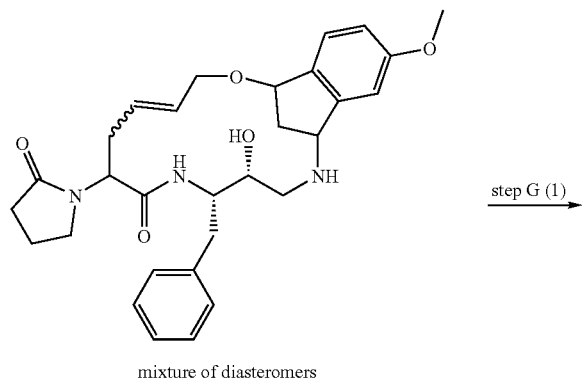

mixture of diasteromers step G (1)

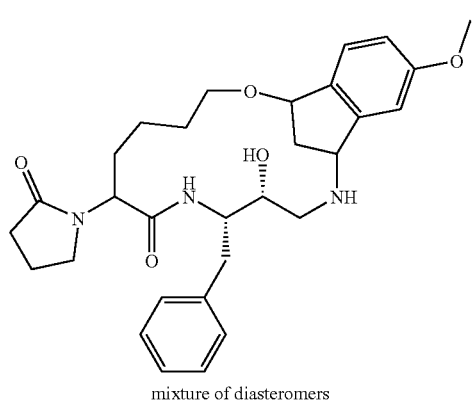

mixture of diasteromers

Step G (1): 10% Palladium on carbon (50 mg) was added to a round-bottom flask charged with a solution of the olefin mixture (46 mg, 0.0886 mmol) form stepF(2) in MeOH (15 mL) under N₂. Evacuated and flushed with H₂. Stirred the mixture under H₂ balloon overnight. Filtered through Celite and concentrated the filtrate. The crude product was purified using reverse phase preparatory HPLC. The fractions containing product were neutralized with solid NaHCO₃ prior to concentration in vacuo. Water was added to the solid residue, the aqueous mixture was extracted with EtOAc, the organic layers were dried over Na₂SO₄, filtered and concentrated in vacuo to provide 15.1 mg (33% yield) of the title compound as a mixture of four diastereomers: LC-MS (M+H)⁺=522.46; HRMS (M+H)⁺=522.2968; ¹H NMR (500 MHz, DMSO-d₆) δ 6.58-7.56 (m, 8H), 3.86-5.00 (m, 4H), 3.78 (s, 3H), 3.40-3.77 (m, 3H), 2.55-3.28 (m, 5H), 0.77-2.45 (m, 13H).

EXAMPLE 3

(1S,4R,5S,8S,14R)-5-(3,5-Difluoro-benzyl)-4-hydroxy-18-methoxy-8-(2-oxo-pyrrolidin-1-yl)-13-oxa-2,6-diaza-tricyclo[12.6.1.0$^{15,20}$]henicosa-10,15(20),16,18-tetraen-7-one

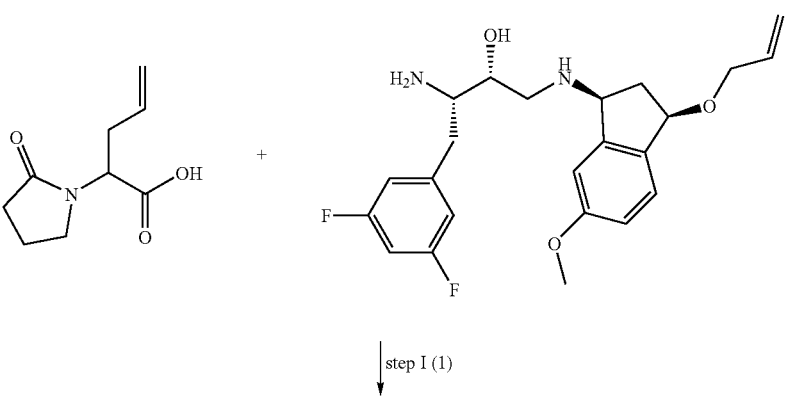

step I (1)

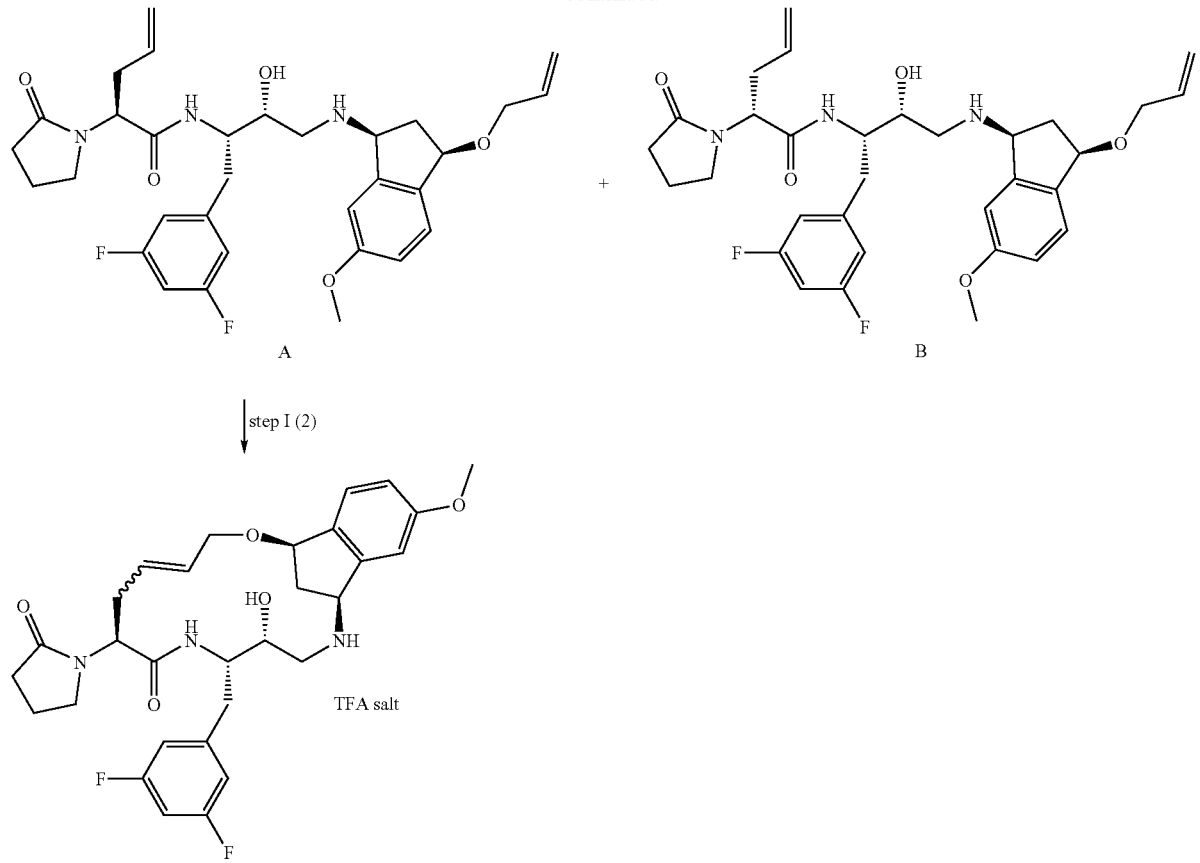

Step I (1): A mixture of (2R,3S)-1-((1S,3R)-3-(allyloxy)-6-methoxy-2,3-dihydro-1H-inden-1-ylamino)-3-amino-4-(3,5-difluorophenyl)butan-2-ol (73 mg, 0.183 mmol) from stepE(2), 2-(2-oxopyrrolidin-1-yl)pent-4-enoic acid (35 mg, 0.192 mmol) from stepA(2), EDC (35 mg, 0.183 mmol), HOBt (25 mg, 0.192 mmol), DIEA (0.155 mL, 0.870 mmol) in 3 mL of DMF were stirred at room temperature for 18 h. The crude product was purified using reverse phase preparatory HPLC to provide two diastereomers. The fractions containing products were neutralized with solid NaHCO$_3$ prior to concentration in vacuo. Water was added to the solid residues, the aqueous mixtures were extracted with EtOAc, the organic layers were dried over Na$_2$SO$_4$, filtered and concentrated in vacuo to provide 28.4 mg (28% yield) of (S)—N-((2S,3R)-4-((1S,3R)-3-(allyloxy)-6-methoxy-2,3-dihydro-1H-inden-1-ylamino)-1-(3,5-difluorophenyl)-3-hydroxybutan-2-yl)-2-(2-oxopyrrolidin-1-yl)pent-4-enamide (diastereomer A, first to elute) and 38.6 mg (38% yield) of (R)—N-((2S,3R)-4-((1S,3R)-3-(allyloxy)-6-methoxy-2,3-dihydro-1H-inden-1-ylamino)-1-(3,5-difluorophenyl)-3-hydroxybutan-2-yl)-2-(2-oxopyrrolidin-1-yl)pent-4-enamide (diastereomer B, second to elute). Data for diastereomer A: LC-MS (M+H)$^+$=584.37, HRMS (M+H)$^+$=584.2927; $^1$H NMR (500 MHz, CDCl$_3$) δ 7.30 (d, J=8.24 Hz, 1H), 6.91 (d, J=2.14 Hz, 1H), 6.83 (dd, J=8.24, 2.44 Hz, 1H), 6.65-6.80 (m, J=6.10, 6.10 Hz, 2H), 6.54-6.68 (m, 2H), 5.85-6.06 (m, 1H), 5.51-5.72 (m, 1H), 5.31 (dd, J=17.24, 1.68 Hz, 1H), 5.18 (dd, J=10.38, 1.53 Hz, 1H), 4.94-5.12 (m, 2H), 4.77 (dd, J=6.26, 4.43 Hz, 1H), 4.52 (dd, J=9.00, 6.56 Hz, 1H), 3.96-4.24 (m, 4H), 3.79 (s, 3H), 3.39-3.59 (m, 1H), 3.03-3.35 (m, 2H), 2.75-2.93 (m, 2H), 2.46-2.76 (m, 4H), 2.20-2.40 (m, 2H), 2.07-2.22 (m, 1H), 1.79-1.96 (m, 2H), 1.66-1.81 (m, 1H). Data for diastereomer B: LC-MS (M+H)$^+$= 584.97; HRMS (M+H)$^+$=584.2955; $^1$H NMR (500 MHz, CDCl$_3$) δ 7.29 (d, J=8.54 Hz, 1H), 6.97-7.13 (m, 1H), 6.89-6.97 (m, 1H), 6.83 (dd, J=8.39, 2.29 Hz, 1H), 6.73 (m, 2H), 6.57-6.67 (m, 1H), 5.80-6.05 (m, 1H), 5.41-5.59 (m, 1H), 5.24-5.39 (m, 1H), 5.17 (d, J=10.38 Hz, 1H), 4.88-5.10 (m, 2H), 4.67-4.84 (m, 1H), 4.35 (dd, J=8.55, 7.02 Hz, 1H), 3.96-4.23 (m, 4H), 3.70-3.87 (m, 3H), 3.50-3.64 (m, 1H), 3.24-3.45 (m, 2H), 3.00 (dd, J=14.19, 4.12 Hz, 1H), 2.80 (dd, J=12.21, 3.36 Hz, 1H), 2.54-2.76 (m, 3H), 2.39-2.55 (m, 1H), 2.19-2.43 (m, 3H), 1.75-1.99 (m, 3H).

Step I (2): The TFA salt of (S)—N-((2S,3R)-4-((1S,3R)-3-(Allyloxy)-6-methoxy-2,3-dihydro-1H-inden-1-ylamino)-1-(3,5-difluorophenyl)-3-hydroxybutan-2-yl)-2-(2-oxopyrrolidin-1-yl)pent-4-enamide (diastereomer A, 10 mg, 0.0143 mmol) from stepG(1) was dissolved in 2 mL of CH$_2$CL$_2$. Added Hoveyda/Grubbs catalyst [(1,3-bis-(2,4,6-trimethylphenyl)-2-imidazolidinylidene)dichloro(O-isoproproxylphenylmethylene)ruthenium] (2.4 mg, 2.9 μmol, Aldrich) and stirred at room temperature overnight. Evaporated to dryness. Dissolved in MeOH and filtered. The crude product was purified using reverse phase preparatory HPLC to give 5.5 mg (70% yield) of the title compound as its TFA salt: LC-MS (M+H)$^+$=556.31; HRMS (M+H)$^+$=556.2603; $^1$H NMR (500 MHz, CDCl$_3$) δ 7.27-7.43 (m, 1H), 7.04-7.21 (m, 1H), 6.99 (d, J=8.24 Hz, 1H), 6.40-6.83 (m, 3H), 5.42-5.79 (m, 2H), 4.98 (d, J=5.49 Hz, 1H), 4.71 (d, J=5.49 Hz, 1H), 4.25-4.51 (m, 1H), 4.06 (d, J=8.24 Hz, 1H), 3.87-4.06 (m, 2H), 3.72-3.91 (m, 3H), 3.36-3.72 (m, 3H), 3.16-3.39 (m, 2H), 3.06-3.21 (m, 1H), 2.92-3.08 (m, 1H), 2.76-2.89 (m, 1H), 2.54-2.76 (m, 2H), 2.17-2.54 (m, 3H), 1.86 (dd, J=14.34, 7.32 Hz, 2H), 0.91-1.52 (m, 2H).

EXAMPLE 4

(1S,4R,5S,8S,14R)-8-((S)-3-Butyl-2-oxo-pyrrolidin-1-yl)-5-(3,5-difluoro-benzyl)-4-hydroxy-18-methoxy-13-oxa-2,6-diaza-tricyclo[12.6.1.0^{15,20}]henicosa-10,15(20),16,18-tetraen-7-one

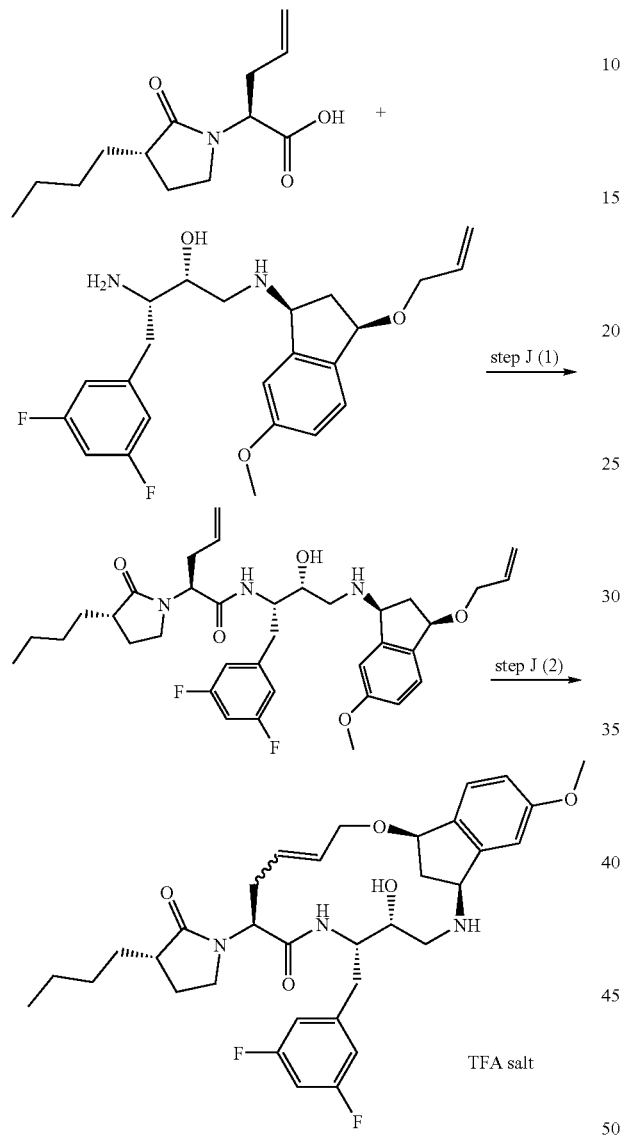

Step J (1): A mixture of (2R,3S)-1-((1S,3R)-3-(allyloxy)-6-methoxy-2,3-dihydro-1H-inden-1-ylamino)-3-amino-4-(3,5-difluorophenyl)butan-2-ol (51 mg, 0.122 mmol) from stepE(2), (S)-2-((S)-3-butyl-2-oxopyrrolidin-1-yl)pent-4-enoic acid (31 mg, 0.128 mmol) from stepB(5), EDC (25 mg, 0.128 mmol), HOBt (17 mg, 0.128 mmol), and DIEA (108 μL, 0.610 mmol) were mixed in 2 mL of DMF and stirred at room temperature for 24 h. Purified using reverse phase preparatory HPLC to give 61 mg of (S)—N-((2S,3R)-4-((1S,3R)-3-(allyloxy)-6-methoxy-2,3-dihydro-1H-inden-1-ylamino)-1-(3,5-difluorophenyl)-3-hydroxybutan-2-yl)-2-((S)-3-butyl-2-oxopyrrolidin-1-yl)pent-4-enamide as clear viscous residue (TFA salt). A 2 mg sample was free based by passage through basic alumina (activated, Brockmann I), using methanol as an eluant: LC-MS (M+H)+=640.6; 1H NMR (500 MHz, CDCl3) δ 7.27-7.37 (m, 1H), 6.78-6.93 (m, 2H), 6.69-6.80 (m, 2H), 6.55-6.67 (m, 1H), 5.81-6.08 (m, 1H), 5.52-5.72 (m, 1H), 5.31 (dd, J=17.09, 1.53 Hz, 1H), 5.18 (dd, J=10.38, 1.22 Hz, 1H), 4.91-5.14 (m, 2H), 4.65-4.86 (m, 1H), 4.49 (dd, J=9.77, 6.10 Hz, 1H), 3.97-4.22 (m, 3H), 3.75-3.87 (m, 3H), 3.34-3.55 (m, 1H), 2.99-3.33 (m, 2H), 2.84-3.00 (m, 1H), 2.53-2.86 (m, 4H), 2.19-2.52 (m, 2H), 2.00-2.19 (m, 1H), 1.69-1.93 (m, 2H), 1.42-1.72 (m, 5H), 1.17-1.40 (m, 5H), 0.98-1.15 (m, 1H), 0.79-0.96 (m, 3H).

Step J (2): Hoveyda-Grubb's catalyst [(1,3-bis-(2,4,6-trimethylphenyl)-2-imidazolidinylidene)dichloro(O-isopropoxylphenylmethylene)ruthenium] (6.6 mg, 7.8 μmol, Aldrich) was added to flask charge with a solution of (S)—N-((2S,3R)-4-((1S,3R)-3-(allyloxy)-6-methoxy-2,3-dihydro-1H-inden-1-ylamino)-1-(3,5-difluorophenyl)-3-hydroxybutan-2-yl)-2-((S)-3-butyl-2-oxopyrrolidin-1-yl)pent-4-enamide (59 mg, 0.0783 mmol, TFA salt) from stepH(1) in CH2Cl2 at room temperature. The mixture was stirred for 3 days. The resulting solution was evaporated to dryness, dissolved in MeOH, and filtered through Celite. Purified using reverse phase preparatory HPLC to give 26.2 mg (46% yield) of the title compound as a TFA salt: LC-MS (M+H)+=612.51; 1H NMR (500 MHz, CDCl3) δ 7.35 (d, J=8.55 Hz, 1H), 7.14 (s, 1H), 6.92-7.10 (m, 2H), 6.41-6.80 (m, 3H), 5.59-5.74 (m, 1H), 5.43-5.57 (m, 1H), 4.78-5.16 (m, 4H), 4.72 (d, J=5.49 Hz, 1H), 4.40 (d, J=9.77 Hz, 1H), 3.98-4.16 (m, 2H), 3.66-3.98 (m, 4H), 3.07-3.39 (m, 3H), 2.47-2.85 (m, 3H), 2.24-2.50 (m, 2H), 1.93-2.20 (m, 2H), 1.68-1.88 (m, 1H), 1.05-1.53 (m, 6H), 0.74-0.94 (m, 3H).

EXAMPLE 5

(1S,4R,5S,8S,14R)-8-((S)-3-Butyl-2-oxo-pyrrolidin-1-yl)-5-(3,5-difluoro-benzyl)-4-hydroxy-18-methoxy-13-oxa-2,6-diaza-tricyclo[12.6.1.0^{15,20}]henicosa-15(20),16,18-trien-7-one

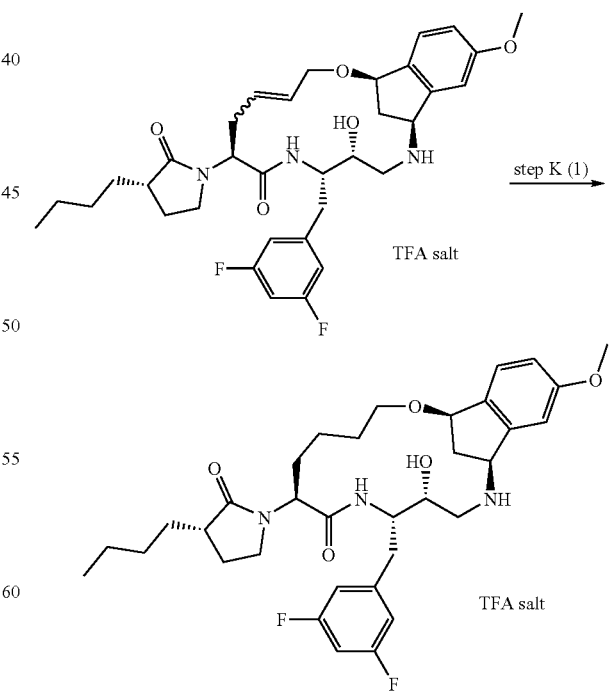

Step K (1): 10% Palladium on carbon (14 mg) was added to a round-bottom flask charged with a solution of the olefin mixture (46 mg, 0.0886 mmol) form stepF(2) in MeOH under $N_2$. Evacuated and flushed with $H_2$. Stirred the mixture under $H_2$ balloon overnight. Filtered through Celite and concentrated the filtrate. Purified the crude product using reverse phase preparatory HPLC to afford 11 mg (79% yield) of the title compound as a TFA salt: LC-MS $(M+H)^+$=614.54; $^1$H NMR (500 MHz DMSO-$d_6$) δ 7.32 (d, J=8.55 Hz, 1H), 7.21 (s, 1H), 7.05-7.17 (m, 1H), 6.96 (dd, J=8.55, 2.14 Hz, 1H), 6.48-6.81 (m, 2H), 4.90 (d, J=7.63 Hz, 1H), 4.66 (d, J=6.41 Hz, 1H), 4.16-4.43 (m, 1H), 3.98-4.19 (m, 1H), 3.82-4.00 (m, 1H), 3.75-3.85 (m, 3H), 3.38-3.76 (m, 2H), 2.85-3.40 (m, 6H), 2.36-2.84 (m, 4H), 2.17-2.44 (m, 2H), 1.99-2.19 (m, 1H), 1.86-2.02 (m, 1H), 1.66-1.85 (m, 1H), 1.48-1.68 (m, 1H), 1.04-1.43 (m, 9H), 0.88 (t, J=6.71 Hz, 3H).

EXAMPLE 6

N—[(S)-1-((1S,4R,5S,8S,14R)-5-Benzyl-4-hydroxy-18-methoxy-7-oxo-13-oxa-2,6-diaza-tricyclo[12.6.1.0$^{15,20}$]henicosa-10,15(20),16,18-tetraen-8-yl)-3-sec-butyl-2-oxo-pyrrolidin-3-yl]-acetamide

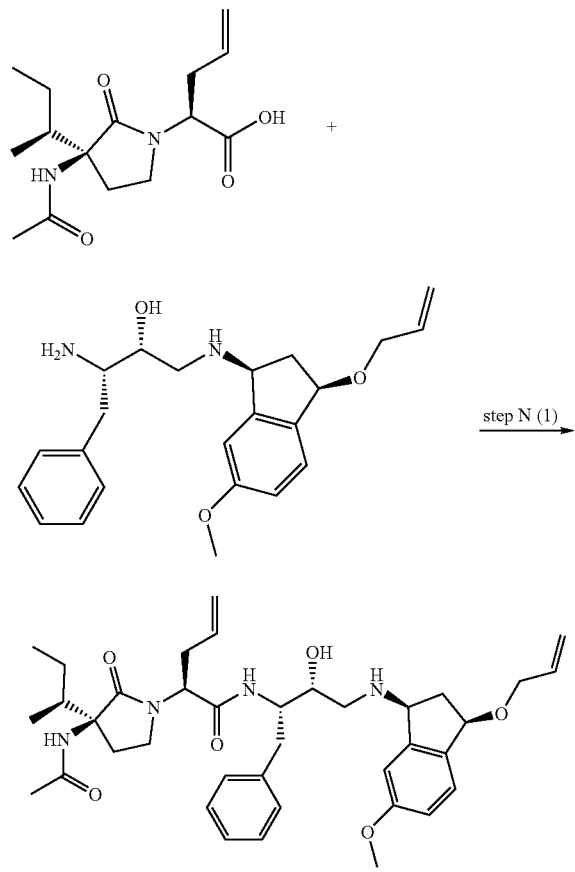

step N (1)

step N (2)

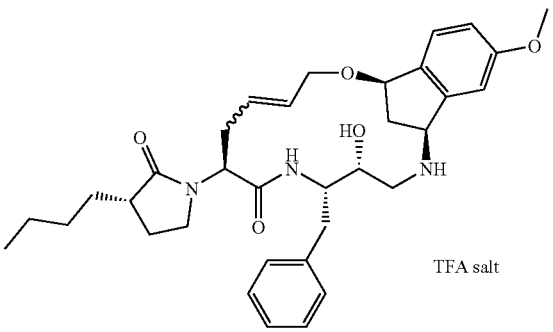

TFA salt mixture of cis- and trans- olefins

Step N (1): (2R,3S)-1-((1S,3R)-3-(allyloxy)-6-methoxy-2,3-dihydro-1H-inden-1-ylamino)-3-amino-4-(3,5-difluorophenyl)butan-2-ol (20 mg, 0.05 mmol) from step E (2), (S)-2-((S)-3-acetamido-3-sec-butyl-2-oxopyrrolidin-1-yl) pent-4-enoic acid (14 mg, 0.048 mmol) from step L (7), EDC (10 mg, 0.05 mmol), HOBt (7 mg, 0.05 mmol), DIEA (40 μL, 0.24 mmol) were mixed in 2 mL of DMF. The mixture was stirred at RT for 24 h. Purified with reverse phase Prep-HPLC to give 14.1 mg of (S)-2-((S)-3-acetamido-3-sec-butyl-2-oxopyrrolidin-1-yl)-N-((2S,3R)-4-((1S,3R)-3-(allyloxy)-6-methoxy-2,3-dihydro-1H-inden-1-ylamino)-3-hydroxy-1-phenylbutan-2-yl)pent-4-enamide as a light brown viscous residue (TFA salt): LC-MS $(M+H)^+$=661.37, $^1$H NMR (300 MHz, CDCl$_3$) δ ppm 0.82 (t, J=5.86 Hz, 2H) 0.89-1.69 (m, 5H) 1.86-2.04 (m, 4H) 2.35-2.90 (m, 5H) 3.05-4.17 (m, 19H) 4.57 (d, J=6.59 Hz, 1H) 4.75 (d, J=4.76 Hz, 1H) 4.87-4.98 (m, 1H) 5.12-5.34 (m, 1H) 5.38-5.57 (m, 1H) 5.78-5.94 (m, 1H) 6.01 (s, 1H) 6.84-6.95 (m, 1H) 7.02-7.36 (m, 8H) 7.70 (d, J=9.15 Hz, 1H).

Step N (2): Hoveyda-Grubb's 2nd generation catalyst (1.7 mg, 2.0 μmol) was added to flask charge with a solution of (S)-2-((S)-3-acetamido-3-sec-butyl-2-oxopyrrolidin-1-yl)-N-((2S,3R)-4-((1S,3R)-3-(allyloxy)-6-methoxy-2,3-dihydro-1H-inden-1-ylamino)-3-hydroxy-1-phenylbutan-2-yl) pent-4-enamide (15.5 mg, 0.020 mmol, TFA salt) from step N (1) in dichloroethane at 50° C. The mixture was stirred for 16 h. Evaporated to dryness. Dissolved in MeOH and filtered. Purified with reverse phase Prep-HPLC to give 7.4 mg (50%) of the N—[(S)-1-((1S,4R,5S,8S,14R)-5-Benzyl-4-hydroxy-18-methoxy-7-oxo-13-oxa-2,6-diaza-tricyclo[12.6.1.0$^{15,20}$]henicosa-10,15(20),16,18-tetraen-8-yl)-3-sec-butyl-2-oxo-pyrrolidin-3-yl]-acetamide as the TFA salt: LC-MS $(M+H)^+$=633.29, HRMS $(M+H)^+$=633.3652; $^1$H NMR (300 MHz, CDCl$_3$) δ ppm 0.49 (d, J=5.12 Hz, 1H) 0.60-1.04 (m, 3H) 1.13-1.38 (m, 3H) 1.41-1.71 (m, 1H) 1.90-2.30 (m, 3H) 2.51 (s, 1H) 2.84 (d, J=1.83 Hz, 3H) 3.06-3.39 (m, 2H) 3.45-4.89 (m, 21H) 5.65 (s, 1H) 6.55 (s, 1H) 6.92-7.52 (m, 8H).

EXAMPLE 7

(1S,4R,5S,8S,14R)-5-Benzyl-4-hydroxy-8-((S)-3-isobutyl-2-oxo-pyrrolidin-1-yl)-18-methoxy-13-oxa-2,6-diaza-tricyclo[12.6.1.0$^{15,20}$]henicosa-10,15(20),16,18-tetraen-7-one

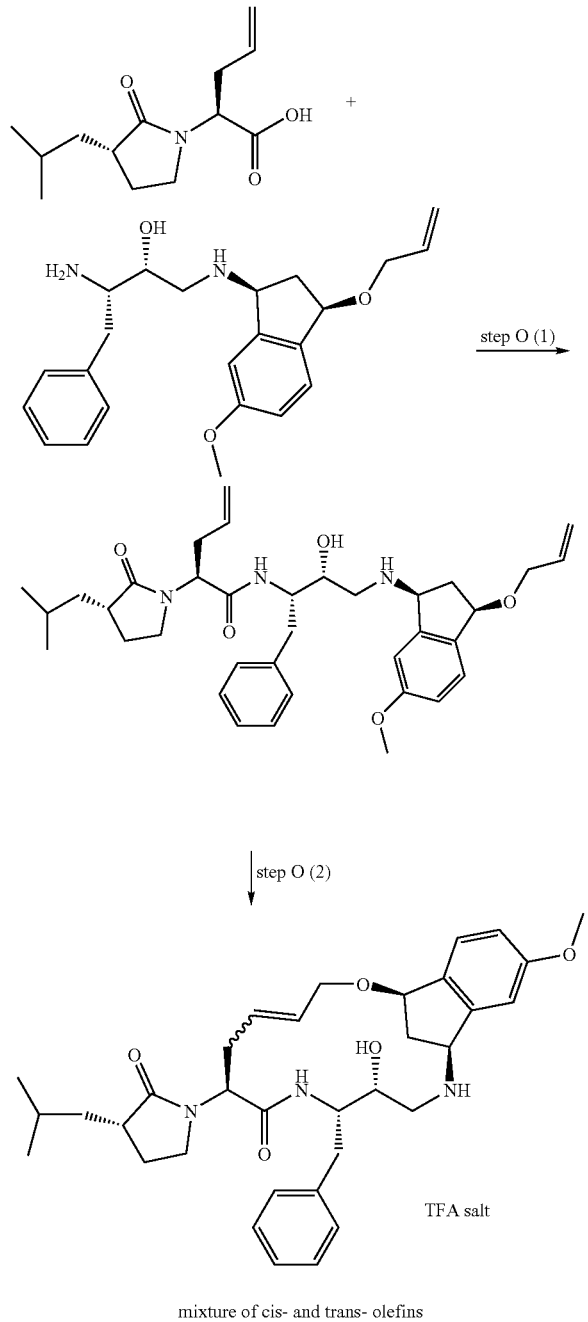

mixture of cis- and trans- olefins

Step O (1): (2R,3S)-1-((1S,3R)-3-(Allyloxy)-6-methoxy-2,3-dihydro-1H-inden-1-ylamino)-3-amino-4-(3,5-difluorophenyl)butan-2-ol (20 mg, 52.3 µmol) from step E (2), (S)-2-((S)-3-isobutyl-2-oxopyrrolidin-1-yl)pent-4-enoic acid (12.5 mg, 52.3 µmol) from step M (5), EDC (10 mg, 52.3 µmol), HOBt (7.1 mg, 52.3 µmol), DIEA (46.7 µL, 262 µmol) were mixed in 1 mL of DMF. The mixture was stirred at RT for 24 h. Purified with reverse phase Prep-HPLC to give 28.2 mg of (S)—N-((2S,3R)-4-((1S,3R)-3-(allyloxy)-6-methoxy-2,3-dihydro-1H-inden-1-ylamino)-3-hydroxy-1-phenylbutan-2-yl)-2-((S)-3-isobutyl-2-oxopyrrolidin-1-yl)pent-4-enamide as the TFA salt: LC-MS (M+H)$^+$=603.3 HRMS (M+H)$^+$=604.3755 1H NMR (500 MHz, CDCl$_3$) δ ppm 0.80-0.96 (m, 6H) 1.08 (dd, J=10.53, 8.70 Hz, 1H) 1.23-1.38 (m, 1H) 1.54-1.66 (m, 2H) 1.96-2.06 (m, 1H) 2.26-2.45 (m, 3H) 2.51-2.77 (m, 3H) 2.85-2.95 (m, 1H) 3.03-3.16 (m, 2H) 3.28 (d, J=11.90 Hz, 1H) 3.76-3.84 (m, 3H) 3.92 (d, J=1.83 Hz, 1H) 4.03-4.12 (m, 2H) 4.20-4.29 (m, 1H) 4.46 (dd, J=10.22, 5.34 Hz, 1H) 4.73 (d, J=6.41 Hz, 1H) 4.78-4.87 (m, 1H) 4.95-5.07 (m, 2H) 5.21 (d, J=10.38 Hz, 1H) 5.30 (dd, J=17.40, 1.53 Hz, 1H) 5.54 (dd, J=14.80, 7.78 Hz, 1H) 5.84-5.98 (m, 1H) 6.71 (s, 1H) 6.95 (dd, J=8.24, 2.14 Hz, 1H) 7.11-7.28 (m, 6H) 7.34 (d, J=8.24 Hz, 1H).

Step O(2): Hoveyda-Grubb's 2nd generation catalyst (3.01 mg, 3.55 µmol) was added to flask charge with a solution of (S)—N-((2S,3R)-4-((1S,3R)-3-(allyloxy)-6-methoxy-2,3-dihydro-1H-inden-1-ylamino)-3-hydroxy-1-phenylbutan-2-yl)-2-((S)-3-isobutyl-2-oxopyrrolidin-1-yl)pent-4-enamide (25.5 mg, 35.5 µmol, TFA salt) from step O (1) in DCM (4 mL) at RT. The mixture was stirred for 16 h. Evaporated to dryness. Dissolved in MeOH and filtered. Purified with reverse phase Prep-HPLC to give 17.9 mg (75%) of the (1S,4R,5S,8S,14R)-5-Benzyl-4-hydroxy-8-((S)-3-isobutyl-2-oxo-pyrrolidin-1-yl)-18-methoxy-13-oxa-2,6-diaza-tricyclo[12.6.1.0$^{15,20}$]henicosa-10,15(20),16,18-tetraen-7-one as the TFA salt: LC-MS (M+H)$^+$=576.2, HRMS (M+H)$^+$=576.3447; $^1$H NMR (500 MHz, CDCl$_3$) δ ppm 0.91 (dd, J=32.81, 5.95 Hz, 4H) 1.11 (t, J=9.77 Hz, 1H) 1.30-1.44 (m, 1H) 1.55-1.72 (m, 2H) 2.03 (dd, J=13.12, 4.58 Hz, 2H) 2.28-2.76 (m, 12H) 3.14 (s, 3H) 3.72-3.92 (m, 3H) 4.04-4.19 (m, 2H) 4.40 (s, 1H) 4.72 (d, J=4.58 Hz, 1H) 4.83-4.96 (m, 1H) 5.51-5.74 (m, 1H) 6.92-7.30 (m, 8H) 7.35 (t, J=8.39 Hz, 1H).

BIOLOGICAL METHODS

There are a number of methods by which inhibitors of the BACE enzyme can be identified experimentally. The enzyme can be obtained from membrane samples from natural tissues or cultured cells or can be expressed recombinantly in a host cell by well known methods of molecular biology. The whole enzyme or a portion thereof can be expressed, for example, in bacterial, insect or mammalian cells to obtain a catalytically active enzyme species. The enzymatic activity and/or ligand binding capability of the enzyme can be assessed within these membrane samples, or the enzyme can be purified to varying extents. As an illustrative example, the nucleic acid sequence encoding the pro and catalytic domains of human BACE can be appended on the 5' end with an untranslated and signal sequence from the gene for acetylcholinesterase, and on the 3' end with a sequence encoding a poly-histidine tag. This cDNA can then be expressed in Drosophila melanogaster S2 cells in which the signal and pro sequences of the transcribed/translated protein are removed by cellular proteases and the catalytic domain, appended by a C-terminal poly-histidine tag, is secreted out into the cellular medium. The enzyme can then be purified from the culture medium by nickel affinity chromatography by methods well known to those trained in the art [Mallender, W. et al., "Characterization of recombinant, soluble beta-secretase from an insect cell expression system." Mol. Pharmacol. 2001, 59: 619-626]. Similar strategies for expressing and purifying various forms of BACE in bacterial, mammalian and other cell types would be known to one skilled in the art. A preferred method for determining the potency of a test compound in binding to the BACE enzyme is by moitoring the displacement of a suitable radioligand.

Radioligand displacement assays with a radiolabeled BACE inhibitor (WO 2004 013098, compound 3, where the methoxy group is substituted for C(3H)$_3$) were carried out using standard methods (Keen, M. (1999) in *Receptor Binding Techniques* (Walker, J. M. ed) p. 106 Humana Press, Totowa, N.J.). The HEK293-9B.A1 cell line, which overexpresses the BACE1 enzyme, was derived from HEK293 cells (Simmons, N. L. (1990) A cultured human renal epithelioid cell line responsive to vasoactive intestinal peptide. *Exp. Physiol.* 75:309-19.) by RAGE™ (Harrington, J. J. et al. (2001) Creation of genome-wide protein expression libraries using random activation of gene expression. *Nat. Biotechnol.* 19:440-5.; U.S. Pat. Nos. 6,410,266 and 6,361,972). T225 flask cultures of HEK293-9B.A1 were grown to 80% confluency in DMEM supplemented with 2 mM L-glutamine, 10 μg/ml penicillin, 10 μg/ml streptomycin, 3 μg/ml puromycin, 100 nM methotrexate, and 10% fetal bovine serum (Invitrogen, Carlsbad, Calif.), harvested, and resuspended at 2×10$^8$ cells per 10 ml of lysis buffer consisting of 50 mM HEPES pH 7.0 containing a protease inhibitor cocktail of AEBSF 104 μM, aprotinin 80 nM, leupeptin 2 μM, bestatin 4 μM, pepstatin A 1.5 μM, and E-64 1.4 μM (0.1% of protease inhibitor cocktail P8340, Sigma-Aldrich, St. Louis, Mo.) at 4° C. The resuspended cells were homogenized using a Polytron (Brinkman, Westbury, N.Y.) at setting 6 for 10 sec., then centrifuged at 48,000×g for 10 min. The resulting pellet was washed by repeating the resuspension, homogenization and centrifugation steps. The final pellet was resuspended in buffer at 4° C. to yield a total protein concentration of 5 mg/ml, then aliquots were frozen in liquid nitrogen for further storage at –70° C. Immediately before carrying out a binding assay, an aliquot of cell homogenate was thawed and diluted to a concentration of 100 μg/ml in assay buffer consisting of 50 mM HEPES pH 5.0 and 0.1% CHAPSO. Assays were initiated in polypropylene 96-well plates (Costar, Cambridge, Mass.) by the addition of 200 μl of cell homogenate to 50 μl of assay buffer containing 1 nM radioligand (WO 2004 013098, compound 3, where the methoxy group is substituted for C($^3$H)$_3$: 80 Ci/mMol) and various concentrations of unlabelled compounds, and incubated for 1.5 hr. at 25° C. Separation of bound from free radioligand was by filtration on GFF glass fiber filters (Innotech Biosystems International, Lansing, Mich.) using an Innotech cell harvester. Filters were washed three times with 0.3 ml of phosphate buffered saline pH 7.0 at 4° C. and assessed for radioactivity using a Wallac 1450 Microbeta liquid scintillation counter (PerkinElmer, Boston, Mass.). Ki values of competing compounds were derived through Cheng-Prussoff correction of IC$_{50}$ values calculated using XLfit (IDBS, Guildford, UK).

Abbreviations:

AEBSF: 4-(2-Aminoethyl)benzenesulfonyl fluoride hydrochloride

CHAPSO: 3-[(3-Cholamidopropyl)dimethylammonio]-2-hydroxy-1-propanesulfonate

D-MEM: Dulbecco's modified eagle medium

HEPES: 4-(2-Hydroxyethyl)piperazine-1-ethanesulfonic acid

RAGE™: Random Activation of Gene Expression™

The activity of specific compounds described herein and tested in the above assay is provided in Table 1.

TABLE 1

| Compound of Example | Activity Rating[a] |
|---|---|
| 1 | + |
| 2 | + |
| 3 | ++ |
| 4 | +++ |
| 5 | +++ |
| 6 | +++ |
| 7 | +++ |

[a]Activity based on IC$_{50}$ values:
+++ = <0.01 μM
++ = 0.01-1.0 μM
+ = >1.0 μM In Vitro Assay to Identify β-Secretase Inhibitor Based on the Inhibition of Aβ Formation from Membrane Preparations.

An isolated membrane fraction which contains functionally active β-secretase and β-APP substrates can generate β-secretase cleavage products including Aβ (Roberts, S. B.; Hendrick, J. P.; Vinitsky, A.; Lewis, M.; Smith, D. W.; Pak, R. PCT Publication WO 01/0175435; Fechteler, K.; Kostka, M.; Fuchs, M. Patent Application No. DE 99-19941039; Shearman, M.; Beher, D. et al., *Biochemistry*, 2000, 39, 8698-8704; Zhang, L. Song, L. et al., *Biochemistry* 2001, 40, 5049-5055). An isolated membrane fraction can be prepared from human derived cell lines such as HeLa and H4 which have been transfected with wild type or mutant forms of β-APP or a human alkaline phosphatase β-APP fusion construct, and stably express high levels of β-secretase substrates. The endogenous β-secretase present in the isolated membranes prepared at 0-4° C. cleaves the β-APP substrates when the membranes are shifted from 0-4 to 37° C. Detection of the cleavage products including Aβ can be monitored by standard techniques such as immunoprecipitation (Citron, M.; Diehl, T. S. et al., *Proc. Natl. Acad. Sci. USA*, 1996, 93, 13170-13175), western blot (Klafki, H.-W.; Ambramowski, D. et al., *J. Biol. Chem.* 1996, 271, 28655-28659), enzyme linked immunosorbent assay (ELISA) as demonstrated by Seubert, P.; Vigo-Pelfrey, C. et al., *Nature*, 1992, 359, 325-327, or by a preferred method using time-resolved fluorescence of the homogeneous sample containing membranes and Aβ (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000, 39, 8698-8704). The Aβ present in a homogeneous sample containing membranes can be detected by time-resolved fluorescence with two antibodies that recognize different epitopes of Aβ. One of the antibodies recognizes an epitope that is present in Aβ but not present in the precursor fragments; preferably the antibody binds the carboxyl terminus of AD generated by the β-secretase cleavage. The second antibody binds to any other epitope present on Aβ. For example, antibodies that bind the N-terminal region (e.g., 26D6-B2-B3® SIBIA Neurosciences, La Jolla, Calif.) or bind the C-terminal end (e.g., 9S3.2® antibody, Biosolutions, Newark, Del.) of the Aβ peptide are known. The antibodies are labeled with a pair of fluorescent adducts that transfer fluorescent energy when the adducts are brought in close proximity as a result of binding to the N- and C-terminal ends or regions of Aβ. A lack of fluorescence is indicative of the absence of cleavage products, resulting from inhibition of β-secretase. The isolated membrane assay can be used to identify candidate agents that inhibit the activity of β-secretase cleavage and Aβ production.

A typical membrane-based assay requires 45 μg membrane protein per well in a 96- or 384-well format. Membranes in a neutral buffer are combined with the test compound and shifted from 0-4 to 37° C. Test agents may typically consist of synthetic compounds, secondary metabolites from bacterial or fungal fermentation extracts, or extracts from plant or marine samples. All synthetic agents are initially screened at doses ranging from 10-100 μM or in the case of extracts at sufficient dilution to minimize cytotoxicity. Incubation of the membranes with the test agent will continue for approximately 90 minutes at which time fluorescence labeled antibodies are added to each well for AD quantitation. The time-resolved fluorescence detection and quantitation of Aβ is described elsewhere (Roberts, S. B.; Hendrick, J. P.; Vinitsky, A.; Lewis, M.; Smith, D. W.; Pak, R. PCT Publication WO 01/0175435; Shearman, M.; Beher, D. et al., *Biochemistry*, 2000. 39, 8698-8704). Results are obtained by analysis of the plate in a fluorescence plate reader and comparison to the mock treated membranes and samples in which known amounts of Aβ were added to construct a standard concentration curve. A positive acting compound is one that inhibits the Aβ relative to the control sample by at least 50% at the initial tested concentration. Compounds of the present application are considered active when tested in the above assay if the $IC_{50}$ value for the test compound is less than 50 μM. A preferred $IC_{50}$ value is less than 1 μM. A more preferred $IC_{50}$ value is less than 0.1 μM. If a compound is found to be active then a dose response experiment is performed to determine the lowest dose of compound necessary to elicit the inhibition of the production of Aβ.

In Vivo Assays for the Determination of Aβ Reduction by a β-Secretase Inhibitor.

In vivo assays are available to demonstrate the inhibition of β-secretase activity. In these assays, animals, such as mice, that express normal levels of APP, β- and γ-secretase or are engineered to express higher levels of APP and hence Aβ can be used to demonstrate the utility of β-secretase inhibitors, as demonstrated with γ-secretase inhibitors [Dovey, H. et al., (2001), J. Neurochem. 76: 173-181]. In these assays, β-secretase inhibitors are administered to animals and Aβ levels in multiple compartments, such as plasma, cerebral spinal fluid, and brain extracts, are monitored for Aβ levels using methods previously outlined. For instance, Tg2576 mice, which overexpress human APP, are administered β-secretase inhibitors by oral gavage at doses that will cause measurable Aβ lowering, typically less than 100 mg/kg. Three hours after dosing plasma, brain, and CSF are collected, frozen in liquid nitrogen, and stored at −80° C. until analysis. For Aβ detection, plasma is diluted 15-fold in PBS with 0.1% Chaps while CSF is diluted 15-fold in 1% Chaps with protease inhibitors (5 μg/ml leupeptin, 30 μg/ml aprotinin, 1 mM phenylmethylsulfonylfluoride, 1 μM pepstatin). Brains are homogenized in 1% Chaps with protease inhibitors using 24 ml solution/g brain tissue. Homogenates were then centrifuged at 100,000×g for 1 hr at 4° C. The resulting supernatants were then diluted 10-fold in 1% Chaps with protease inhibitors. Aβ levels in the plasma, CSF, and brain lysate can then be measured using time-resolved fluorescence of the homogenous sample or one of the other methods previously described.

A β-secretase inhibitor is considered active in one of the above in vivo assays if it reduces Aβ by at least 50% at a dosage of 100 mg/kg.

DOSAGE AND FORMULATION

The compounds of the present application can be administered orally using any pharmaceutically acceptable dosage form known in the art for such administration. The active ingredient can be supplied in solid dosage forms such as dry powders, granules, tablets or capsules, or in liquid dosage forms, such as syrups or aqueous suspensions. The active ingredient can be administered alone, but is generally administered with a pharmaceutical carrier. A valuable treatise with respect to pharmaceutical dosage forms is Remington's Pharmaceutical Sciences, Mack Publishing.

The compounds of the present application can be administered in such oral dosage forms as tablets, capsules (each of which includes sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to β-amyloid production or accumulation, such as Alzheimer's disease and Down's Syndrome.

The compounds of this application can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents. They can be administered alone, but generally administered with a pharmaceutical carrier selected on the basis of the chosen route of administration and standard pharmaceutical practice.

The dosage regimen for the compounds of the present application will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. An ordinarily skilled physician or veterinarian can readily determine and prescribe the effective amount of the drug required to prevent, counter, or arrest the progress of the condition.

Advantageously, compounds of the present application may be administered in a single daily dose, or the total daily dosage may be administered in divided doses of two, three, or four times daily.

The compounds for the present application can be administered in intranasal form via topical use of suitable intranasal vehicles, or via transdermal routes, using those forms of transdermal skin patches well known to those of ordinary skill in that art. To be administered in the form of a transdermal delivery system, the dosage administration will, of course, be continuous rather than intermittent throughout the dosage regimen.

In the methods of the present application, the compounds herein described in detail can form the active ingredient, and are typically administered in admixture with suitable pharmaceutical diluents, excipients, or carriers (collectively referred to herein as carrier materials) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or β-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present disclosure can also be administered in the form of liposome delivery systems, such as small unilamellar vesicles, large unilamallar vesicles, and multilamellar vesicles. Liposomes can be formed from a variety of phospholipids, such as cholesterol, stearylamine, or phosphatidylcholines.

Compounds of the present disclosure may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present disclosure may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in Remington's Pharmaceutical Sciences, Mack Publishing Company, a standard reference text in this field.

What is claimed is:
1. A compound of Formula (I); or a stereoisomer thereof

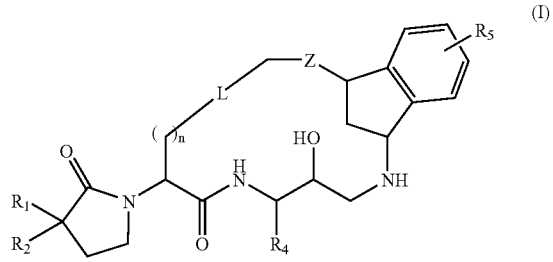

wherein
R$_1$ is hydrogen, C$_{1-6}$alkyl or NHR$_3$;
R$_2$ is hydrogen, C$_{1-6}$alkyl, C$_{3-6}$alkenyl, C$_{3-6}$cycloalkyl or C$_{3-6}$cyloalkyl(C$_{1-4}$alkyl) in which each group is optionally substituted with a group selected from halogen, CF$_3$, CF$_2$H, OH, OCF$_3$ and C$_{1-4}$alkoxy;
R$_3$ is —C(=O)R$_9$, —C(=O)OR$_9$, —C(=O)NHR$_9$, or C$_{1-6}$alkyl optionally substituted with a group selected from C$_{3-6}$cycloalkyl, halogen, CF$_3$, OCF$_3$, OH, C$_{1-4}$alkoxy and CN;
R$_4$ is C$_{1-6}$alkyl, phenyl or phenyl(C$_{1-4}$alkyl) in which each group is optionally substituted with one to two groups selected from halogen, C$_{1-4}$alkyl, OH, CF$_3$, OCF$_3$ and CN;
R$_5$ is hydrogen, halogen, C$_{1-4}$alkyl, OH, C$_{1-4}$alkoxy, CF$_3$, CF$_2$H, OCF$_3$ or CN;
n is 0, 1 or 2;
Z is O or NR$_6$;
R$_6$ is hydrogen or C$_{1-4}$alkyl;
L is —CH(R$_7$)—CH(R$_8$)— or —C(R$_7$)=C(R$_8$)—;
R$_7$ and R$_8$ are each independently hydrogen or methyl; and
R$_9$ is C$_{1-4}$alkyl optionally substituted with the group selected from halogen, OH, CF$_3$, NH$_2$ and C$_{1-4}$alkoxy;
or a nontoxic pharmaceutically acceptable salt thereof.

2. The compound according to claim 1 of Formula (I); or a stereoisomer thereof,

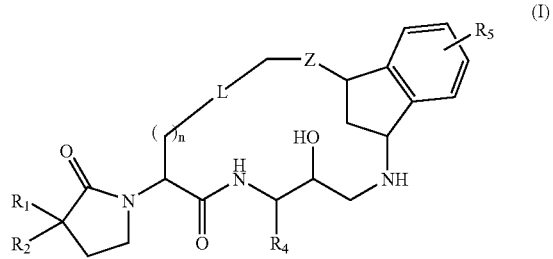

wherein
R$_1$ is hydrogen or NHR$_3$;
R$_2$ is hydrogen, C$_{1-6}$alkyl, C$_{3-6}$alkenyl, C$_{3-6}$cycloalkyl or C$_{3-6}$cyloalkyl(C$_{1-4}$alkyl) in which each group is optionally substituted with a group selected from halogen, CF$_3$, CF$_2$H, OH, and C$_{1-4}$alkoxy;
R$_3$ is —C(=O)R$_9$;
R$_4$ is C$_{1-6}$alkyl, or phenyl(C$_{1-4}$alkyl) in which each group is optionally substituted with one to two groups selected from halogen, C$_{1-4}$alkyl and OH;

$R_5$ is hydrogen, halogen, $C_{1-4}$alkyl, OH, $C_{1-4}$alkoxy, $CF_3$, $CF_2H$, $OCF_3$ or CN;
n is 0, 1 or 2;
Z is O or $NR_6$;
$R_6$ is hydrogen or $C_{1-4}$alkyl;
L is —CH($R_7$)—CH($R_8$)— or —C($R_7$)=C($R_8$)—;
$R_7$ and $R_9$ are each independently hydrogen or methyl; and
$R_9$ is $C_{1-4}$alkyl optionally substituted with the group selected from halogen, OH, $CF_3$, $NH_2$ and $C_{1-4}$alkoxy;
or a nontoxic pharmaceutically acceptable salt thereof.

3. The compound according to claim 2 of formula (Ic);

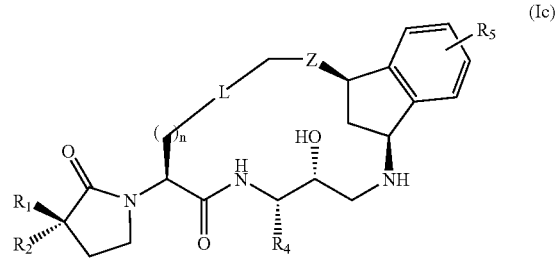

(Ic)

wherein
$R_1$ is hydrogen or $NHR_3$;
$R_2$ is hydrogen, $C_{1-6}$alkyl, $C_{3-6}$alkenyl, $C_{3-6}$cycloalkyl or $C_{3-6}$cyloalkyl($C_{1-4}$alkyl) in which each group is optionally substituted with a group selected from halogen, $CF_3$, $CF_2H$, OH, and $C_{1-4}$alkoxy;
$R_3$ is —C(=O)$R_9$;
$R_4$ is $C_{1-6}$alkyl, or phenyl($C_{1-4}$alkyl) in which each group is optionally substituted with one to two groups selected from halogen, $C_{1-4}$alkyl and OH;
$R_5$ is hydrogen, halogen, $C_{1-4}$alkyl, OH, $C_{1-4}$alkoxy, $CF_3$, $CF_2H$, $OCF_3$ or CN;
n is 0, 1 or 2;
Z is O or $NR_6$;
$R_6$ is hydrogen or $C_{1-4}$alkyl;
L is —CH($R_7$)—CH($R_8$)— or —C($R_7$)=C($R_8$)—;
$R_7$ and $R_8$ are each independently hydrogen or methyl; and
$R_9$ is $C_{1-4}$alkyl optionally substituted with the group selected from halogen, OH, $CF_3$, $NH_2$ and $C_{1-4}$alkoxy;
or a nontoxic pharmaceutically acceptable salt thereof.

4. The compound according to claim 3 of formula (Id);

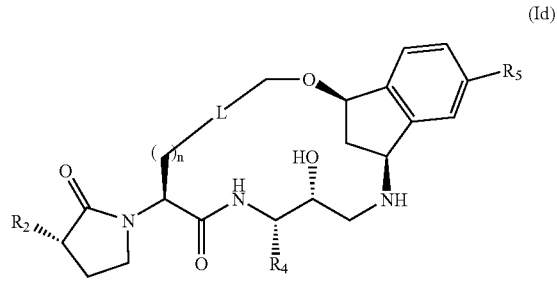

(Id)

$R_2$ is hydrogen, $C_{1-6}$alkyl, $C_{3-6}$cyloalkyl($C_{1-4}$alkyl) in which each group is optionally substituted with a group selected from halogen, $CF_3$, OH, and $C_{1-4}$alkoxy;
$R_4$ is $C_{1-6}$alkyl, or phenyl($C_{1-4}$alkyl) in which each group is optionally substituted with one to two halogen;
$R_5$ is hydrogen, halogen, $C_{1-4}$alkyl, OH, $C_{1-4}$alkoxy, $CF_3$, $CF_2H$, $OCF_3$ or CN;
n is 1 or 2;
L is —CH($R_7$)—CH($R_8$)— or —C($R_7$)=C($R_8$)—; and $R_7$ and $R_8$ are each independently hydrogen or methyl;
or a nontoxic pharmaceutically acceptable salt thereof.

5. The compound according to claim 4 of formula (Id);

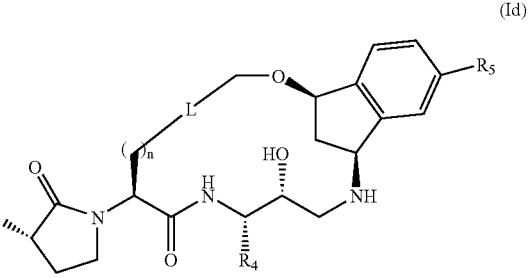

(Id)

wherein
$R_2$ is hydrogen or $C_{1-6}$alkyl;
$R_4$ is benzyl or 3,5-difluorobenzyl;
$R_5$ is hydrogen, $C_{1-4}$alkyl, $C_{1-4}$alkoxy, $CF_3$, $CF_2H$ or $OCF_3$;
n is 1 or 2; and
L is —$CH_2$—$CH_2$— or —CH=CH—;
or a nontoxic pharmaceutically acceptable salt thereof.

6. The compound of claim 1 selected from the group consisting of:

(4R,5S)-5-Benzyl-4-hydroxy-18-methoxy-8-(2-oxo-pyrrolidin-1-yl)-13-oxa-2,6-diaza-tricyclo[12.6.1.0$^{15,20}$]henicosa-10,15(20),16,18-tetraen-7-one;

(4R,5S)-5-Benzyl-4-hydroxy-18-methoxy-8-(2-oxo-pyrrolidin-1-yl)-13-oxa-2,6-diaza-tricyclo[12.6.1.0$^{15,20}$]henicosa-15(20),16,18-trien-7-one;

(1S,4R,5S,8S,14R)-5-(3,5-Difluoro-benzyl)-4-hydroxy-18-methoxy-8-(2-oxo-pyrrolidin-1-yl)-13-oxa-2,6-diaza-tricyclo[12.6.1.0$^{15,20}$]henicosa-10,15(20),16,18-tetraen-7-one;

(1S,4R,5S,8S,14R)-8-((S)-3-Butyl-2-oxo-pyrrolidin-1-yl)-5-(3,5-difluoro-benzyl)-4-hydroxy-18-methoxy-13-oxa-2,6-diaza-tricyclo[12.6.1.0$^{15,20}$]henicosa-10,15(20),16,18-tetraen-7-one;

(1S,4R,5S,8S,14R)-8-((S)-3-Butyl-2-oxo-pyrrolidin-1-yl)-5-(3,5-difluoro-benzyl)-4-hydroxy-18-methoxy-13-oxa-2,6-diaza-tricyclo[12.6.1.0$^{15,20}$]henicosa-15(20),16,18-trien-7-one;

N—[(S)-1-((1S,4R,5S,8S,14R)-5-Benzyl-4-hydroxy-18-methoxy-7-oxo-13-oxa-2,6-diaza-tricyclo[12.6.1.0$^{15,20}$]henicosa-10,15(20),16,18-tetraen-8-yl)-3-sec-butyl-2-oxo-pyrrolidin-3-yl]-acetamide; and (1S,4R,5S,8S,14R)-5-Benzyl-4-hydroxy-8-((S)-3-isobutyl-2-oxo-pyrrolidin-1-yl)-18-methoxy-13-oxa-2,6-diaza-tricyclo[12.6.1.0$^{15,20}$]henicosa-10,15(20),16,18-tetraen-7-one or a nontoxic pharmaceutically acceptable salt thereof.

7. A pharmaceutical composition comprising a therapeutically effective amount of a compound of claim 1 in association with a pharmaceutically acceptable carrier or diluent.

8. A method for the treatment of Alzheimer's Disease which comprises administering to a mammal in need thereof a therapeutically effective amount of a compound of claim 1.

* * * * *